(12) United States Patent
Stanwood et al.

(10) Patent No.: US 10,746,733 B2
(45) Date of Patent: Aug. 18, 2020

(54) MICROFLUIDIC DEVICE HAVING INJECTION-MOLDED FLUIDICS LAYER, AND METHOD OF MAKING SAME

(71) Applicant: ProteinSimple, San Jose, CA (US)

(72) Inventors: Charles Stanwood, San Jose, CA (US); Noel Daigneault, San Jose, CA (US); Jeffrey Branciforte, San Jose, CA (US)

(73) Assignee: PROTEINSIMPLE, San Jose, CA (US)

( * ) Notice: Subject to any disclaimer, the term of this patent is extended or adjusted under 35 U.S.C. 154(b) by 12 days.

(21) Appl. No.: 16/296,618

(22) Filed: Mar. 8, 2019

(65) Prior Publication Data

US 2019/0257827 A1 Aug. 22, 2019

Related U.S. Application Data

(63) Continuation of application No. 15/366,963, filed on Dec. 1, 2016.

(60) Provisional application No. 62/261,456, filed on Dec. 1, 2015.

(51) Int. Cl.
| | |
|---|---|
| *B01L 3/00* | (2006.01) |
| *G05D 7/00* | (2006.01) |
| *C12M 1/40* | (2006.01) |
| *F16K 31/00* | (2006.01) |
| *G01N 33/543* | (2006.01) |
| *G01N 33/53* | (2006.01) |

(52) U.S. Cl.
CPC ...... *G01N 33/54366* (2013.01); *B01L 3/5027* (2013.01); *B01L 3/502715* (2013.01); *B01L 3/502738* (2013.01); *B01L 3/502746* (2013.01); *B01L 2300/021* (2013.01); *B01L 2300/0816* (2013.01); *B01L 2300/0864* (2013.01); *B01L 2300/0867* (2013.01); *B01L 2300/0887* (2013.01); *B01L 2300/123* (2013.01); *B01L 2400/0481* (2013.01); *B01L 2400/0487* (2013.01); *B01L 2400/0655* (2013.01)

(58) Field of Classification Search
CPC ....... B01L 2300/021; B01L 2300/0816; B01L 2300/0864; B01L 2300/0867; B01L 2300/0887; B01L 2300/123; B01L 2400/0481; B01L 2400/0487; B01L 2400/0655; B01L 3/5027; B01L 3/502715; B01L 3/502738; B01L 3/502746; G01N 33/54366
See application file for complete search history.

(56) References Cited

U.S. PATENT DOCUMENTS

2003/0156992 A1* 8/2003 Anderson ......... B01L 3/502707
422/502
2012/0301903 A1* 11/2012 Putnam ............ B01L 3/502707
435/7.92

* cited by examiner

*Primary Examiner* — Jennifer Wecker
(74) *Attorney, Agent, or Firm* — McCormick, Paulding & Huber PLLC

(57) ABSTRACT

A microfluidic device for conducting a fluid assay includes an injection-molded (or "molded") fluidics layer having at least one microfluidic channel configured to allow assay fluids to flow there-along, the channel having channel side walls, a channel bottom, and a channel 3D geometry, and the fluidics layer being made from injection-molded liquid silicone (or PDMS). Having the fluidics layer made from injection molded liquid silicone enables smaller-sized channel features, such as microfluidic valves and pistons, smaller channel dimensions and spacing (providing smaller device footprint, higher device capacity and other benefits), and various geometries for the channels and channel features.

20 Claims, 19 Drawing Sheets

MICROFLUIDIC DEVICE HAVING INJECTION-MOLDED FLUIDICS LAYER, AND METHOD OF MAKING SAME

CROSS REFERENCE TO RELATED APPLICATIONS

This application is a continuation of U.S. patent application Ser. No. 15/366,963, filed Dec. 1, 2016, which claims priority to and the benefit of U.S. Provisional Patent Application Ser. No. 62/261,456, filed Dec. 1, 2015, the entire disclosure of each application above are incorporated herein by reference to the extent permitted by applicable law.

BACKGROUND

It is common practice to perform assays, such as an ELISA (Enzyme Linked Immunosorbent Assay), using a multiwell plate or Microtiter™ plate or microplate, which have multiple small wells, e.g., 96, 384, or 1536, arranged in a 2:3 rectangular matrix. The microplate may be constructed to use the entire plate in an assay, or may provide a capability to use a single row or "strip" of wells out of the microplate matrix, to run a smaller assay. This strip capability permits a single microplate to be used multiple times, using different wells (or groups of wells) each time. In that case, a row or strip of wells may be separated from the matrix and used to run the desired assay. Some products provide a tray, crate or support frame to hold the multiwell plate and the separated strips of wells.

Microplates having "strip" capability (or format) offer the advantage of greater flexibility in testing or diagnostics. They permit the number of tests or assays performed to be adjusted to the number of samples desired to be tested, and not predetermined by the size of the multiwell plate being used.

Examples of multiwell plates having strip capability include: 96 Well Polystyrene Stripwell® Microplate, sold by Corning (including Strip Holder "egg crate" and 96 Well Strip Ejector, and custom multi-color strips); Pierce™ 8-Well Polystyrene Strip Plate, sold by ThermoFisher Scientific; Immulon® Microtiter™ 96-Well Plates and Strips, sold by ThermoScientific (including Removawell™ Assemblies and Strips, and Dividastrips™ Assemblies with 2×8 strips that separate into two 1×8 strips, and Removawell™ Holder that holds eight 12-well or twelve 8-well strips); and 96 Well F8 Strip High Binding ELISA Microplate, sold by Greiner Bio-One GmbH.

However, multi-well plates for running assays are very manual intensive, prone to human error, and do not provide highly precise, repeatable, automated, quantitative assay results for ELISAs and other assays. Thus, it would be desirable to have a device that provides high quality assay results and also provides the scalable flexibility offered by multiwell "strip" capability.

DESCRIPTION

Commonly owned, published US patent applications, publication nos. 2012/0301903 A1, 2015/0086424 A1, 2015/0087558 A1, 2015/0083320 A1, 2015/0083313 A1, 2014/0377146 A1, 2014/0377852 A1, 2015/0087544 A1, 2015/0087559 A1, contain subject matter related to that disclosed herein, each of which are incorporated herein by reference to the extent necessary to understand the present disclosure, as permitted under applicable law.

Figure 1:
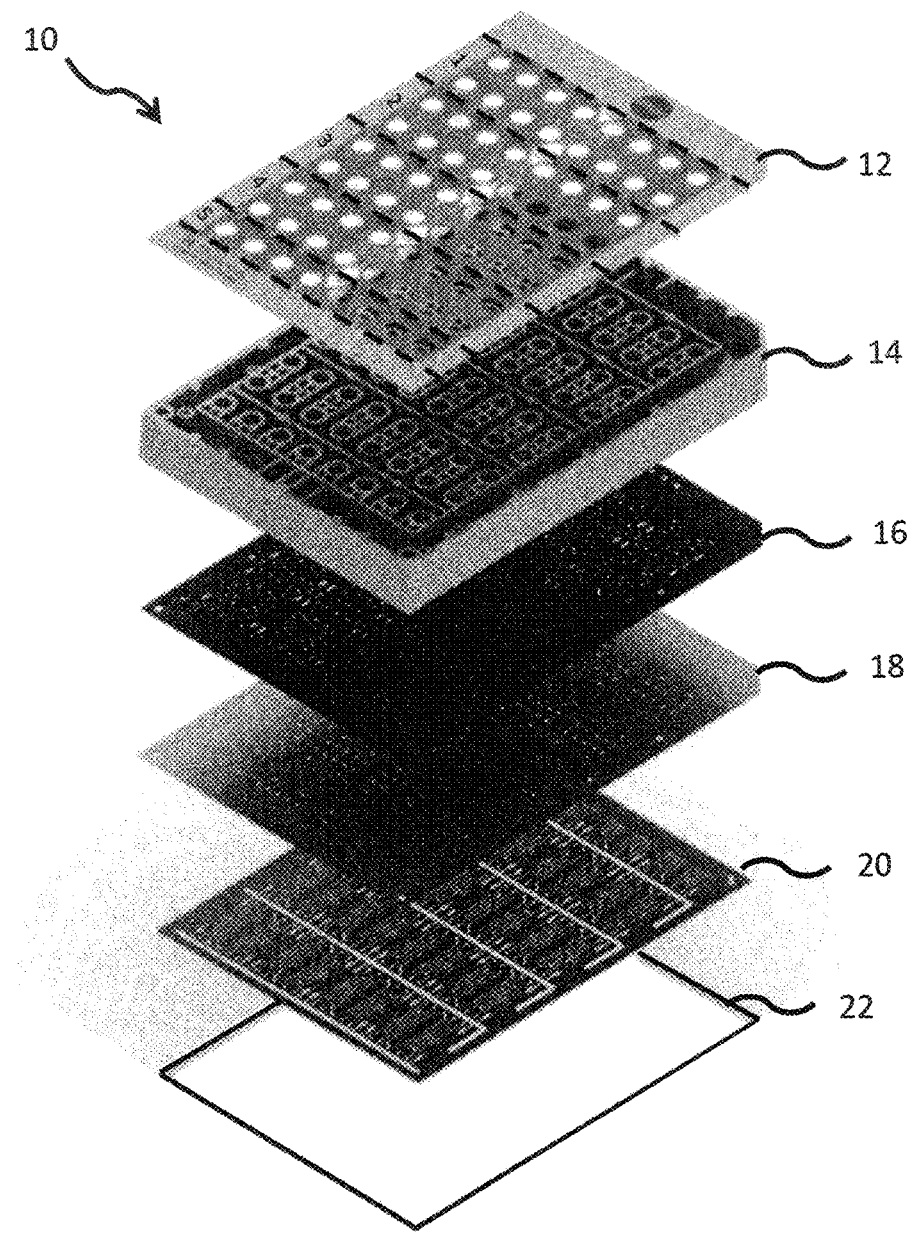
FIG. 1 is an exploded top perspective view of a cartridge for performing an assay, in accordance with embodiments of the present disclosure.
Figure 2:
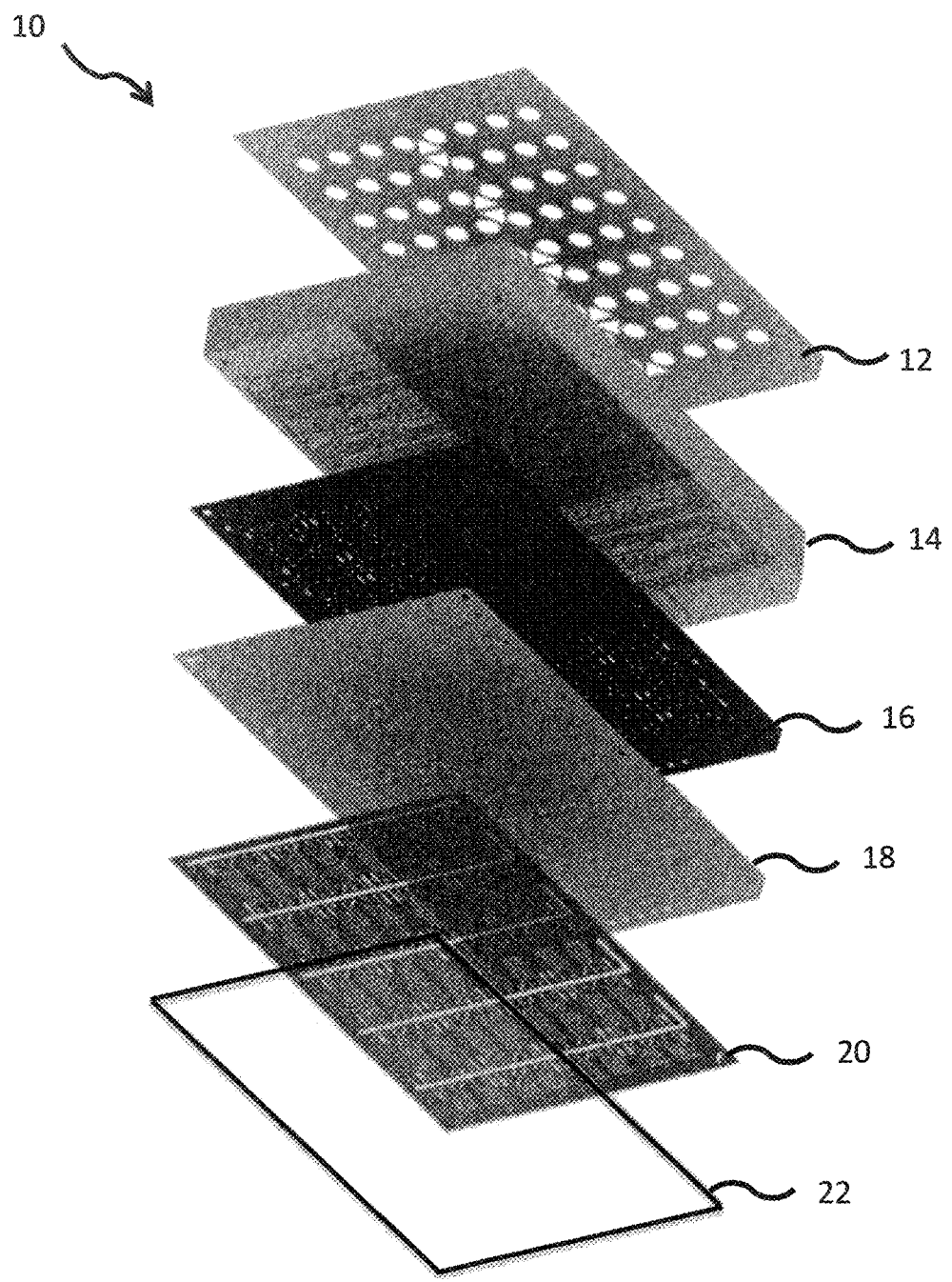
FIG. 2 is an exploded bottom perspective view of the cartridge of FIG. 1, in accordance with embodiments of the present disclosure.

Referring to FIGS. 1 and 2, the multi-use assay cartridge 10 of the present disclosure comprises a plurality of layers 12-22, including, from top to bottom, a label 12, a reservoir layer 14, a control layer 16, a membrane layer 18, a fluidic layer 20 (which includes micro-length tubular flow elements—not shown), and a glass slide layer 22. Other layers may be used if desired, provided it provides the same functions and performance to that described herein. For example, in some embodiments, the glass slide 22 may be eliminated or replaced by another support structure, as discussed herein. During the cartridge assembly process, the layers 12-22 are bonded together or otherwise attached, using various bonding or attachment techniques, to form the cartridge 10, as described further herein and in the aforementioned published patent applications 2015/0086424 A1, 2015/0087558 A1, 2015/0083320 A1, 2015/0083313 A1, 2014/0377146 A1, 2014/0377852 A1, 2015/0087544 A1, 2015/0087559 A1.

All dimensions described herein are shown for exemplary embodiments of the present disclosure, other dimensions, geometries, layouts, and orientations may be used if desired, provided they provide the functions described herein. Also, any dimensions shown on the drawings herein are in millimeters (mm), unless otherwise noted.

The label 12 (or upper-most layer of the cartridge 10) is attached by an adhesive to the top of the reservoir layer 14 and provides a cover or seal for certain wells or reservoirs that hold liquids in the cartridge, such as a common waste reservoir, dye wells, detect analyte wells, and portions of the buffer wells or banks, discussed hereinafter. It also provides access holes for dispensing fluids into the cartridge, such as sample fluid and buffer fluid, to sample wells and buffer wells, as discussed more hereinafter. The label 12 may be partitioned into sections, e.g., 5 sections, shown as numbers 1-5 on the label in FIG. 1, indicative of separate independent assays (or "assay strips") that may be conducted by the cartridge 10, as discussed more hereinafter.

The reservoir layer 14 holds various fluids used in the assay and segregates certain fluids from other fluids to avoid contamination or for other purposes as described herein. The top side of the reservoir layer 14 (FIG. 1) has wells or reservoirs for holding liquids of the assay (e.g., sample, buffer, detect analyte, dye and waste). The bottom side of the reservoir layer 14 (FIG. 2) has pneumatic control lines/channels to control pistons and valves in layers below. The bottom side also has through-holes (or vias) which allow liquids in the wells (on the opposite side) to pass through to the fluidic layer 20 below and allow common waste liquids to pass up to the reservoir layer 14 from the fluidic layer 20 (discussed more hereinafter).

The control layer 16, has holes that allow liquids to pass between the reservoir layer and the fluidic layer, and has other holes that allow pneumatic control lines or pneumatic channels to exert positive and negative pressures on the flexible membrane layer 18 to actuate valves and pistons. The membrane layer 18, is a flexible sheet which acts as a diaphragm for the valves and pistons, and which has holes that allow liquids to pass between the reservoir layer 14 and the fluidic layer 20. The fluidic layer 20 has fluidic channels through which assay fluids flow to perform the assay and which interacts with the membrane layer 18 to create pistons and valves to move fluids through (or along) the channels and interact with micro-length tubular flow elements (or GNRs) to perform the assay. The glass slide layer 22, provides a relatively rigid (or stiff) bottom for the fluidic channels of the fluidic layer 20.

Figure 3:
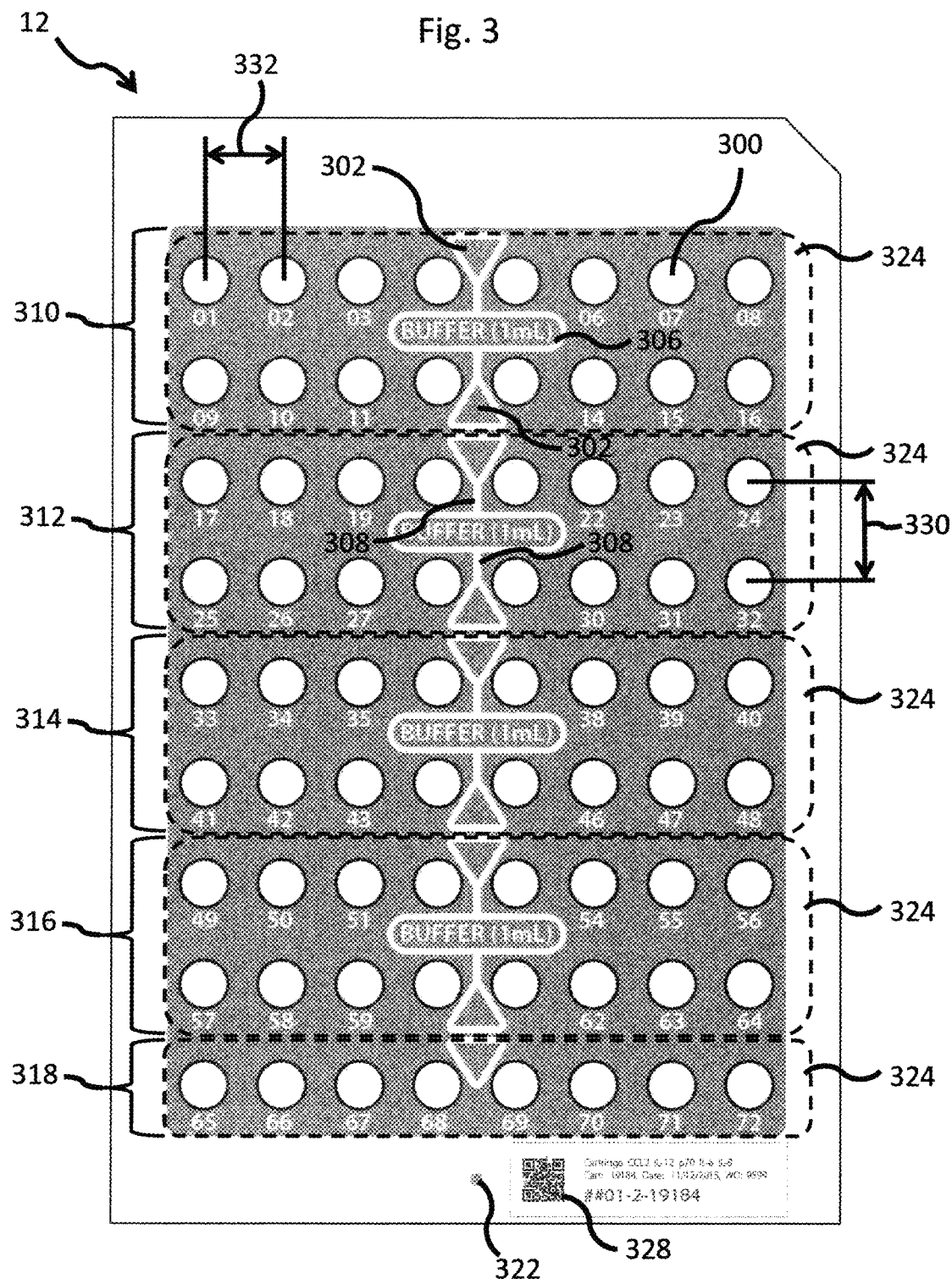
FIG. 3 shows a top view of an upper surface label on the cartridge of FIG. 1, in accordance with embodiments of the present disclosure.

Referring to FIG. 3, more specifically, the label 12 has circular holes 300 that identify openings (or holes) for dispensing (or pipetting or injecting) sample fluid into individual sample wells (72 samples for the example shown) and triangular-shaped holes 302 that identify openings (or holes) for dispensing (or pipetting or injecting) buffer fluid into buffer wells (or banks), discussed more hereinafter. The label 12 also identifies the Sample wells (or ports) by a number 304, e.g., "01" to "72", printed on the label 12 under each of the holes 300 and Buffer wells (or ports) by labels 306, e.g., "BUFFER (1 ml)", and marked lines 308, printed on the label 12 between each row of sample holes 300. These numbers 304 and labels 306,308 provide visual guidance to the user for pipetting sample fluid and buffer fluid into the cartridge 10.

The horizontal distance 332 between the sample holes 300 along one assay strip 310 is about 9 mm, and the vertical distance between sample rows and between samples of adjacent assay strips 310-318, is about 11.5 mm. Also, the overall length of the label 12 is about 126.47 mm and the width of the label 12 is about 84.19 mm. Other distances and dimensions may be used, if desired, provided they meet the functional and performance requirements described herein.

The label 12 may be made of multiple layers of materials, such as polycarbonate, polyester, and selective adhesive, e.g., a hydrophobic adhesive. Other layers, materials and adhesives may be used if desired, provided they provide the same functions and performance to that described herein.

The label 12 may also identify segregated "strips" (or groups) of samples that correspond to assays performed as part of that group, i.e., "assay strips" or "strip assays" 310-318, as discussed more hereinafter. The assay strips 310-318 may also be color-coded or have designs or identifiers on the label 12 to uniquely identify each of the assay strips 310-318.

The label 12 may also have at least one vent hole 322 to ventilate air as needed from within the cartridge, such as from a common waste reservoir (or other portions of the cartridge), e.g., to allow air to escape when waste fluid is pumped into a common waste reservoir, to avoid creating back-pressure in the reservoir.

In some embodiments, the label 12 may have separate removable covers 324 attached to the label, e.g., easy-peel-off plastic (or equivalent) strips or covers, for access to each of the individual assay strips 310-318, which covers the sample holes 300 and the buffer holes 302 for a given strip 310-318, to allow the user to easily identify which assay strips 310-318 have already been used on the cartridge 10, and which of the assay strips 310-318 remain available to use. In some embodiments, the removable/peelable covers 324 may be clear or color-coded, to help identify each of the assay strips and/or which strips 310-318 remain unused. For example, if a user obtains the cartridge 10 and the cover 324 removed for the first assay strip 310 has already been removed, the user then knows to use another assay strip 312-318 on the cartridge 10.

The label 12 may also have one or more bar codes 328 (or other identifying feature) which specifies the details of the assays located on the cartridge 10, e.g., specifying the capture agents and detect analytes that are pre-loaded into the cartridge 10. The cartridge 10 is loaded into an instrument 1400, discussed hereinafter with (FIG. 14), which reads the cartridge bar code 328, controls the assay protocol, optically interrogates the cartridge 10 to obtain the assay results, and provides the assay results to the user. In some embodiments, there may be a bar code (or equivalent) associated with each of the assay strips 310-318 on the cartridge 10, e.g., located within a section of the label 12 associated with each assay strip 310-318, to identify to the instrument 1400 (FIG. 14) which assay strip is being run. In that case, the user would scan the bar code located next to the assay strip into the instrument before running the assay, or the instrument 1400 may read the appropriate bar code(s) automatically. Then the user may select which assay strip to run. The instrument 1400 may also identify which assay strip covers 324 have been previously removed and which assays have been run and indicate same to the user.

Figure 4A:
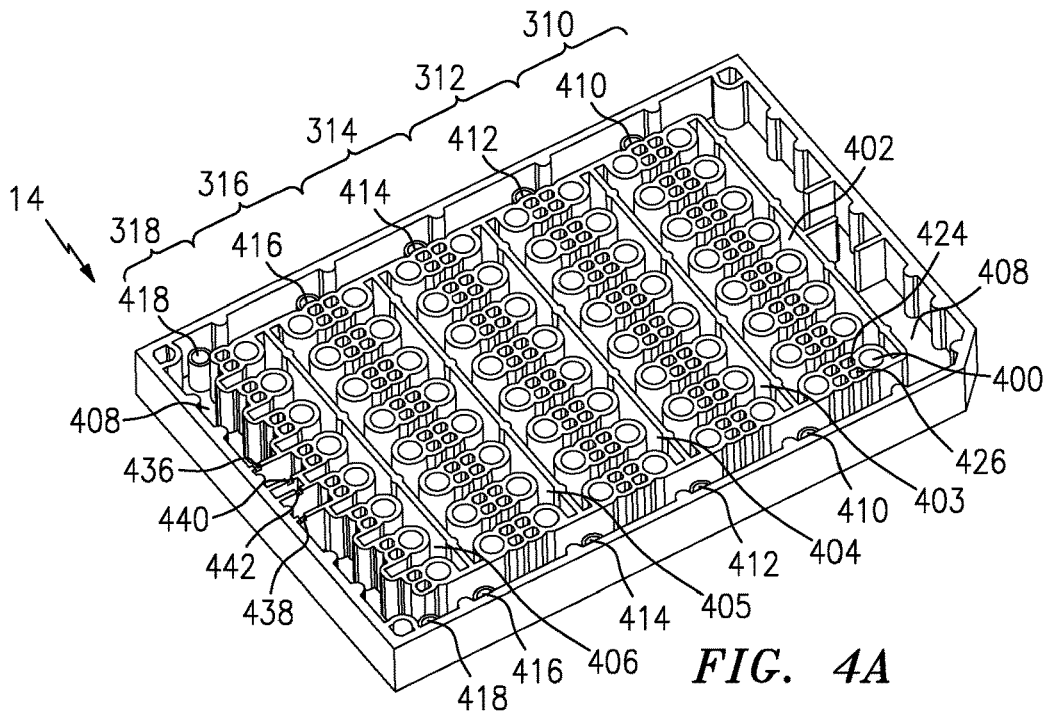
FIG. 4A is a top perspective view of a reservoir layer, in accordance with embodiments of the present disclosure.
Figure 4B:
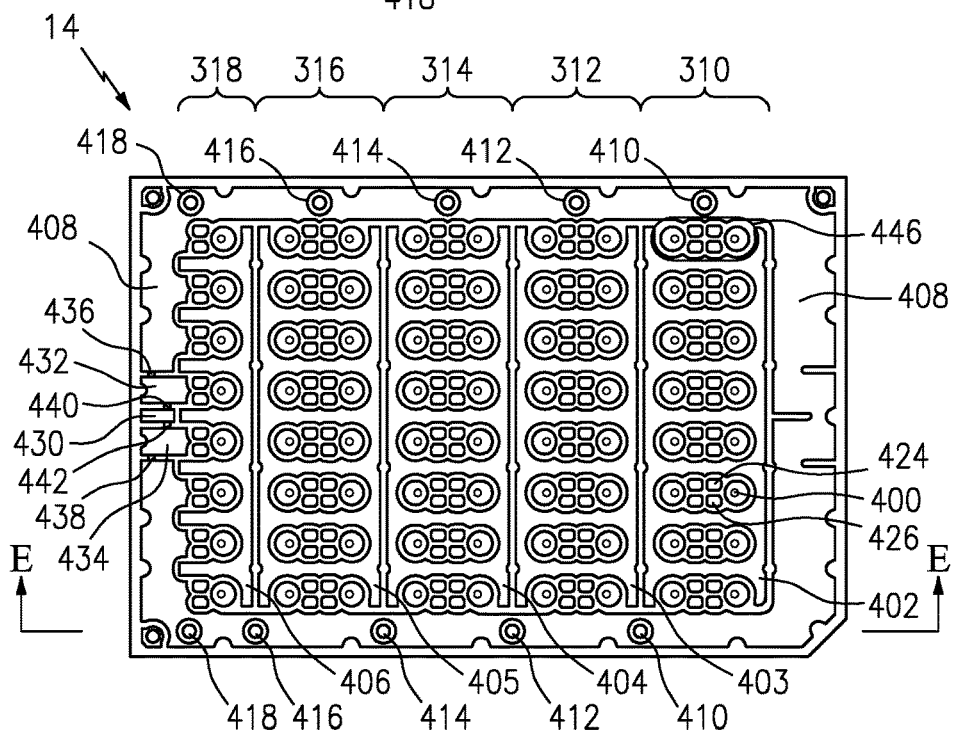
FIG. 4B is a top view of the reservoir layer of FIG. 4A, in accordance with embodiments of the present disclosure.
Figure 4E:
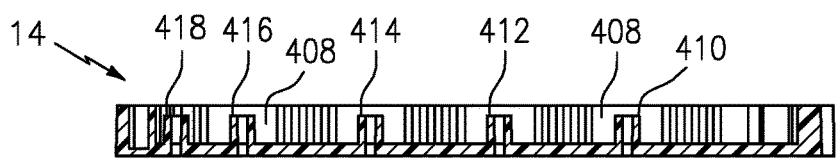
FIG. 4E is a side cut-away view of the cartridge including reservoir layer of FIG. 4B, taken along a line E-E, in accordance with embodiments of the present disclosure.

Referring to FIGS. 4A-4E, the reservoir layer 14 is made of black, rigid plastic such as acrylic or polystyrene, e.g., Styron-498, or the like, and may be injection molded or cast, or drilled out, laser cut, hogged out, or otherwise formed using techniques now known or later developed. Referring to FIGS. 4A, 4B, and 4E, the top side of the reservoir layer 14 has 72 sample wells 400, 5 buffer wells (or banks) 402-406, 72 detect analyte wells 424, 72 dye wells 426, and a common waste reservoir 408. The reservoir layer 14 also has 5 pairs of waste towers (or chimneys) 410-418, (one pair associated with each assay strip 310-318), which allow waste fluid from the fluidics layer 20 to flow into the common waste reservoir 408. FIG. 4E shows a side cut-away or cross section view of the reservoir layer 408 including the waste towers 410-418. It also shows the layers 22-16 underneath the reservoir layer 14.

The reservoir layer 14 also has a vent hold chamber 430 and two antechambers (or pre-chambers) 432,434, in the common waste reservoir 408, which make it difficult for waste fluid in the common waste reservoir 408 to exit the vent hole 332 in the label/cover 12. The vent hole 322 in the cover 12 is located directly above the vent hole chamber 430, which is located between the two antechambers 432, 434. For any waste liquid in the common waste reservoir 408 to escape the cartridge 10, it must first pass through small notches 436,438 at the top of the walls of the antechambers 432,434, respectively, and must then pass through another set of small notches 440,442 at the top of the walls of the vent hole chamber 430. The notches 436-442 in the walls may be staggered as shown in FIGS. 4A and 4B to make it more difficult for liquid to escape or drip out of the cartridge 10.

The thickness of the reservoir layer 14 is about 9 mm. The distance between the sample wells 400 along one row of an assay strip 310 is about 9 mm, and the distance between sample wells 400 between rows for a given assay strip is about 10.818 mm, and the distance between samples wells 400 of adjacent assay strips 310-318, is about 12.182 mm. Also, the overall length of the reservoir layer 14 is about 127.64 mm and the width of the reservoir layer 14 is about 85.42 mm. Other distances and dimensions may be used, if desired, provided they meet the functional and performance requirements described herein.

Figure 4C:
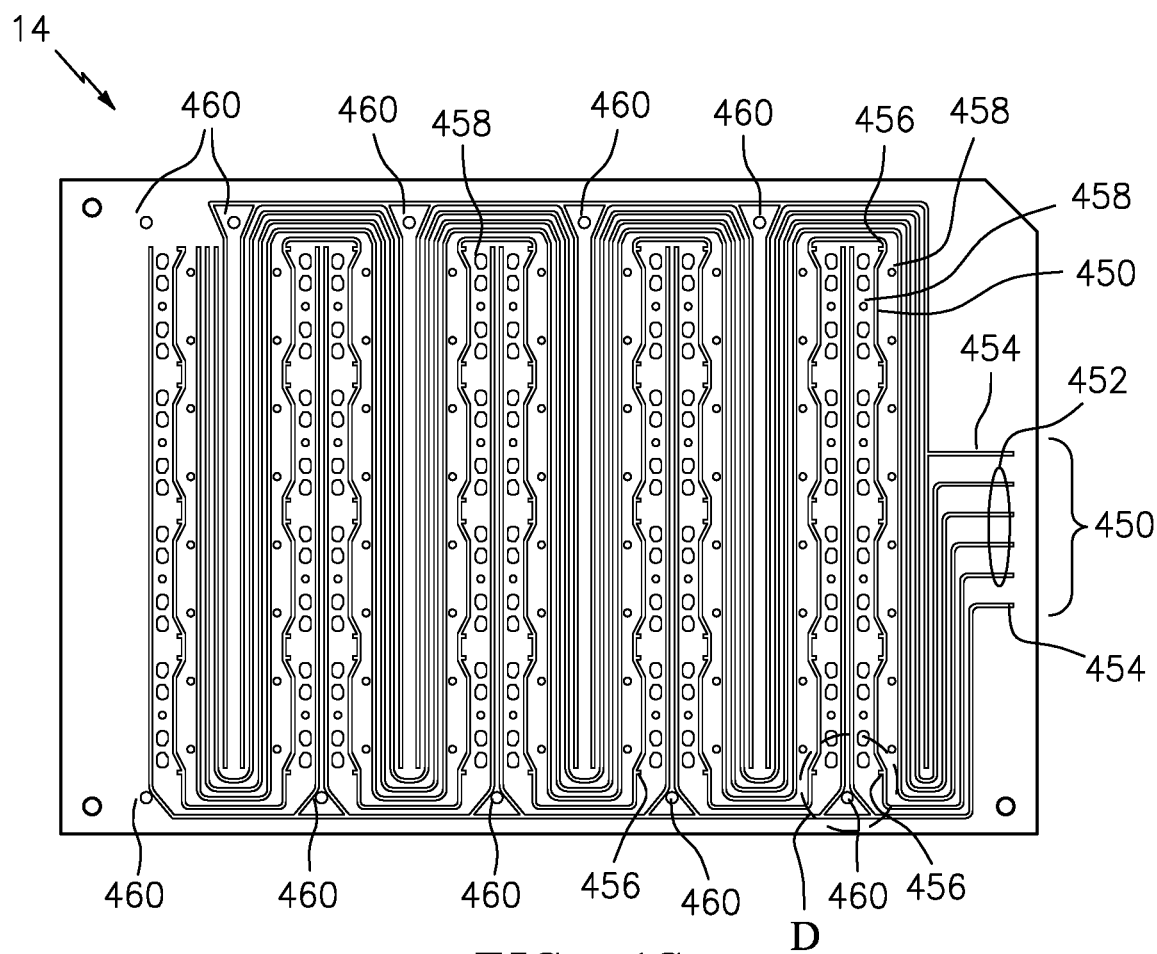
FIG. 4C is a bottom view of the reservoir layer of FIG. 4A, in accordance with embodiments of the present disclosure.
Figure 4D:
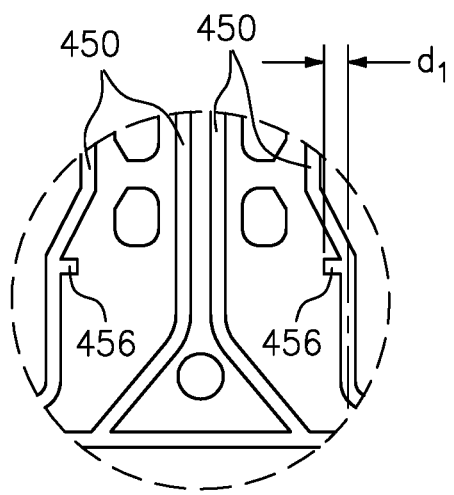
FIG. 4D is a detail view of section of FIG. 4C showing a stub for driving the pistons from one end, in accordance with embodiments of the present disclosure.

Referring to FIGS. 4C and 4D, the bottom side of the reservoir layer 14 has pneumatic control lines or channels 450 to control the pistons and valves in layers below. The control channels 450 may have a serpentine pattern 452 or a parallel or star pattern 454, and may have parallel stubs 456 used for driving the end of the pistons, as discussed more hereinafter. The bottom side of the reservoir layer 14 also has through-holes (or vias) 458, which allow liquids in the wells (on the opposite side) to pass through to the fluidic layer 20 below and through-holes (or vias) 460 that allow common waste liquids to pass up to the reservoir layer 14 from the fluidic layer 20 below (discussed more hereinafter). The pneumatic channels 450, and holes/vias 458,460 may be molded in (e.g., injection molded) or laser cut, drilled out, hogged out, or otherwise created.

The reservoir layer 14 may be formed by a single injection molded process, if desired. The overall size of the reservoir layer 14 may be about 85.42 mm wide and 127.64 mm long, and about 9 mm thick. Other sizes may be used if desired provided they meet the requirements described herein.

Figure 5:
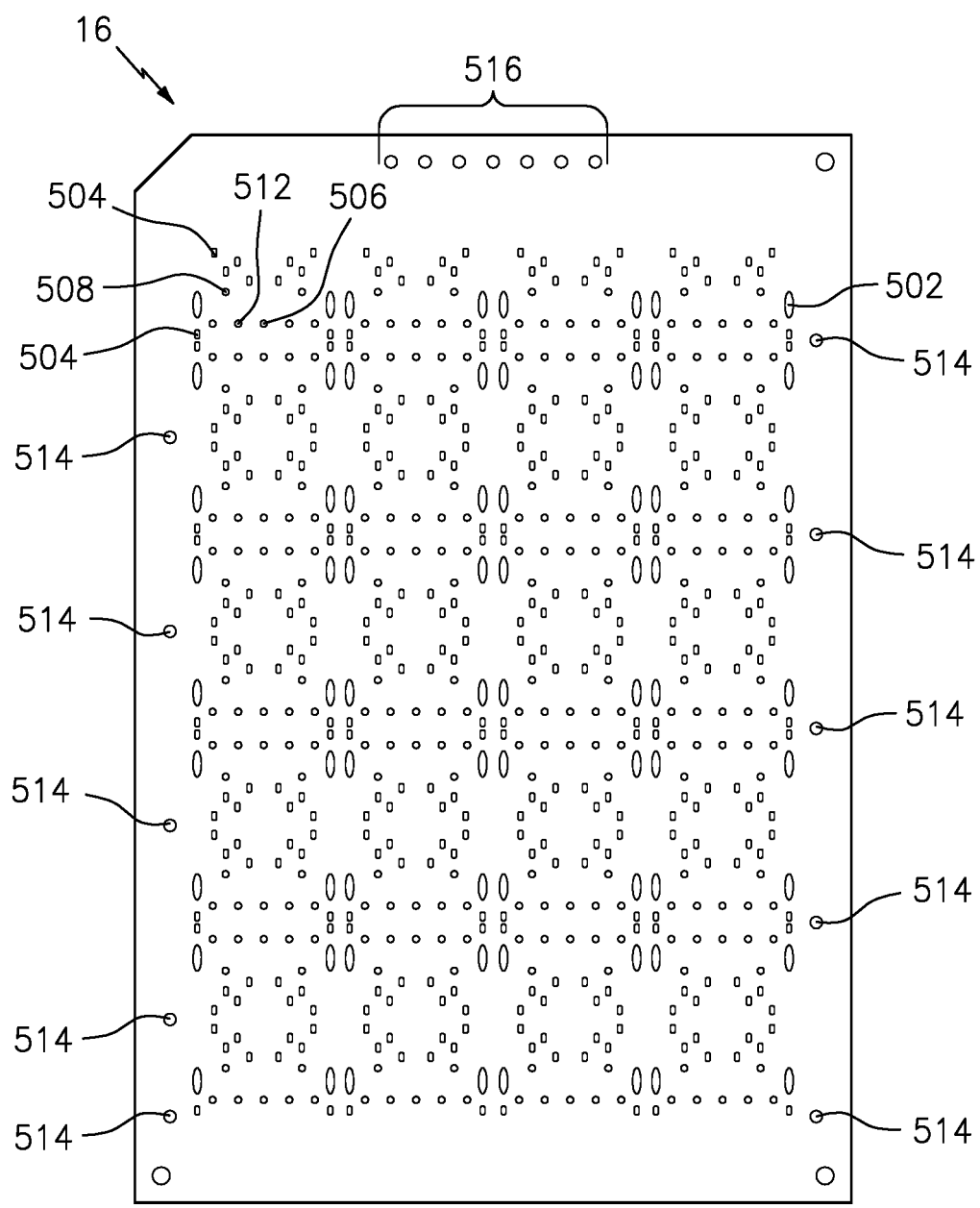
FIG. 5 is a top view of a control layer, in accordance with embodiments of the present disclosure.

Referring to FIG. 5, the control layer 16 has pistons (oval or ellipse-shaped) and valve (semi-rectangular-shaped) cutouts 502,504, respectively, which intersect with pneumatic control lines in the reservoir layer 14 (above it). When vacuum or pressure is applied (from the pneumatic channels 450, FIG. 4C), the pressure pulls or pushes corresponding portions of the flexible membrane layer 18 (below it) into or away from the cutout features 502,504 to control pistons and valves, respectively. The cutouts dimensions for the valves is about 1.0 mm×0.5 mm and for the pistons is an ellipse shape with a length of about 3.0 mm and a width of about 0.8 mm. The control layer 16 forms a barrier between the pneumatics above and the fluidics side below by providing a stiff layer to selectively cover the pneumatic channels 450 (above it) which avoids pushing the flexible membrane 18 into fluidic channels where the fluidic and pneumatic channels cross. The control layer 16 is made of black Lexan® and is coated on both sides with a pressure sensitive adhesive (PSA) or thin acrylic-based adhesive, or the like, to adhere to the reservoir layer 14 above and the membrane layer 18 below. It also blocks fluorescence of the reservoir layer 14 and optically hides the pneumatic channels from the optical sensing system of the instrument 1400 (FIG. 14) during scanning of the cartridge 10 by the instrument.

The control layer 16 also has through-holes (or vias), 506 (buffer), 508 (sample), 510 (detect analyte), 512 (dye), 514 (waste), to allow liquids from the wells (above it) to pass through to layers (below it) and to allow waste liquids from below to pass upward to the reservoir layer 14. In addition, the thickness of the control layer 16 determines the amount or distance of upward movement of the flexible membrane 18 and thus contributes to the piston 502 volume. Accordingly, to make the piston volume larger or smaller, the thickness of the control layer 16 may be increased or decreased, respectively. The thickness of the control layer 16 is approximately 126 microns. However, other thicknesses may be used if desired. The piston volume for the cartridge 10 of the present disclosure is approximately 600 nanoliters. Other piston volumes may be used, if desired, provided the piston provides adequate mixing of the sample liquid with the sample well 400 (FIGS. 4A,4B) and provides adequate force to pump the waste liquid up the waste towers 410-418, and provided it meets the other functional and performance requirements discussed herein. Also, thru-holes 516 along the top edge of the control layer 16 provide pneumatic connection ports to mate with individual male ports on a pneumatic manifold on the instrument 1400 to provide pneumatic pressure/vacuum to the cartridge 10. The overall size of the control layer 16 may be about 84.2 mm wide and 126.48 mm long. Other sizes may be used if desired provided they meet the requirements described herein.

Figure 6:
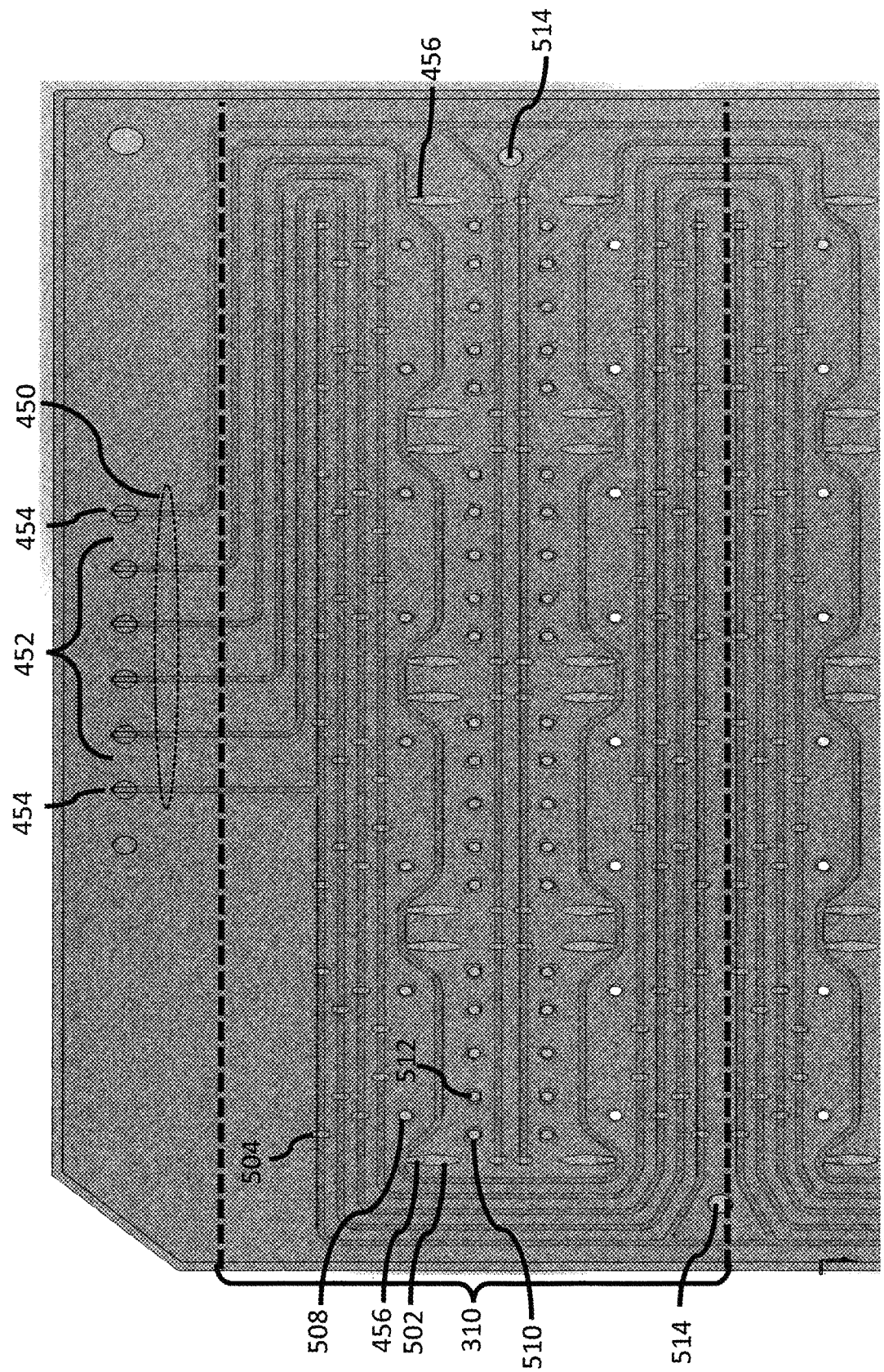
FIG. 6 is a top view of pneumatic and control layers, in accordance with embodiments of the present disclosure.

Referring to FIG. 6, the combination of the pneumatic control lines 450 on the bottom of the reservoir layer 14 and the through-holes (or vias) (e.g., 506 (buffer), 508 (sample), 510 (detect analyte), 512 (dye), 514 (waste)), and cutouts (e.g., pistons 502, valves 504) of the control layer 16 in an enlarged view of the top assay strip 310 is shown, as well as the vias 514 that feed the pair of waste towers 410 for assay strip 310.

Figure 7:
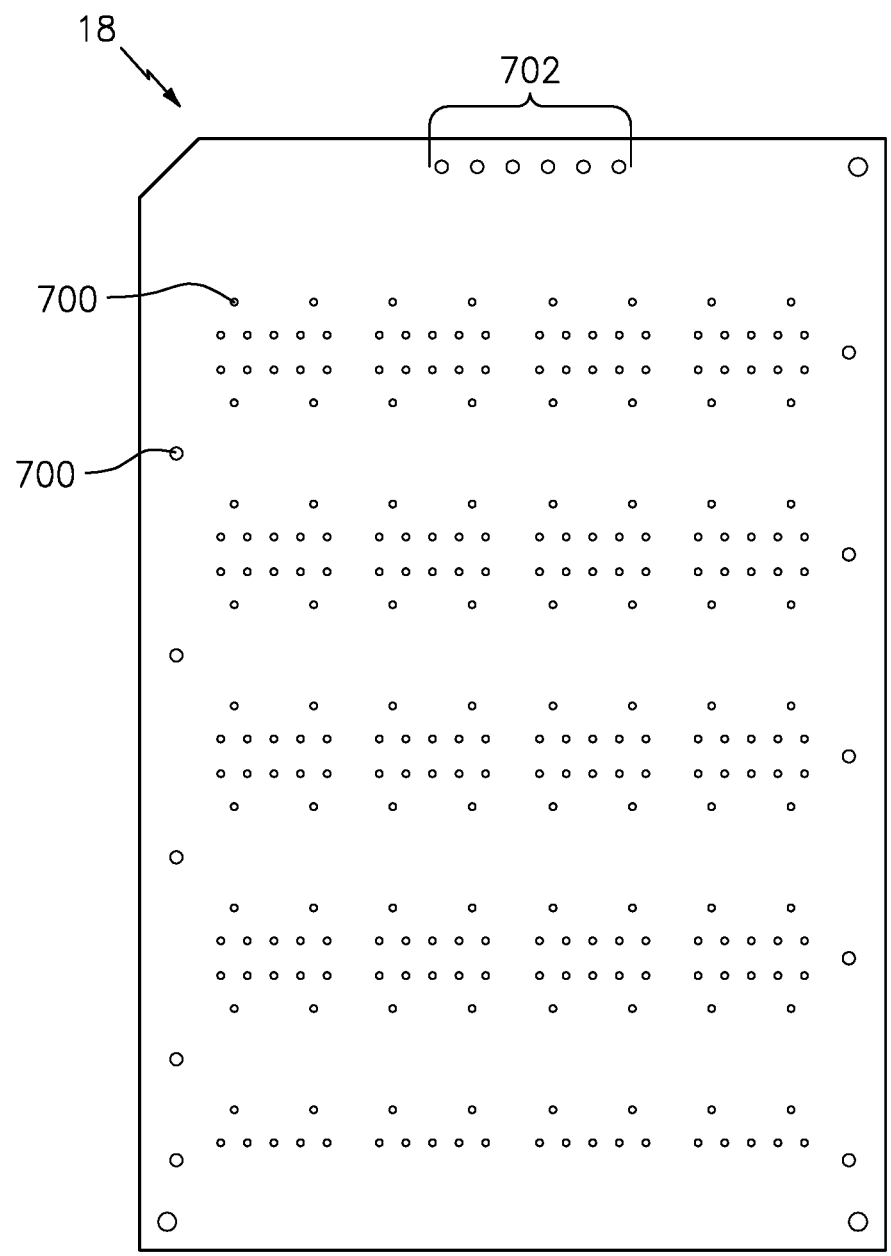
FIG. 7 is a top view of a membrane layer, in accordance with embodiments of the present disclosure.

Referring to FIG. 7, the membrane layer 18 is made of a flexible elastomer material, such as clear PDMS (silicone rubber) or other similar flexible elastomer membrane material as is described in aforementioned commonly-owned published US patent applications. Where piston and valve features are present on adjacent layers (e.g., the control layer 16 cutouts and the fluidic layer 20 fluidic channel geometry), the layer 18 forms flexible membranes over the features that flexes when pressure/vacuum is applied. Portions of the membrane 18 act as pneumatic-actuated flexible membranes (or diaphragms) for the pistons or valves when they interact with corresponding features in the fluidic layer 20. Through-holes (or vias) 700 are also provided to allow liquids from the reservoir layer 14 (above it) to pass through to the fluidic layer 20 (below it) and to allow waste liquids from the fluidic layer 20 to pass upward to the reservoir layer 14.

Through-holes 702 on the top edge of the membrane layer 18 provide a seal to individual pneumatic pressure/vacuum ports on the instrument manifold, which enable the instrument 1400 (FIG. 14) to connect to the pneumatic control channels/lines 450 in the reservoir layer 14 without leaking. Thus, in some embodiments, the flexible elastomer membrane layer 18 also serves to provide a clampable/removable sealed pneumatic connection from the pneumatic supply ports on the instrument 1400 (FIG. 14) to the pneumatic channels 450 on the bottom side of the reservoir layer 14, for providing controllable pneumatic pressure/vacuum to the pneumatic channels 450 to control the valves and pistons. The membrane layer 18 is approximately 110 microns thick, about 84.2 mm wide and about 126.48 mm long. However, other thicknesses and other dimensions may be used if desired.

Figure 8:
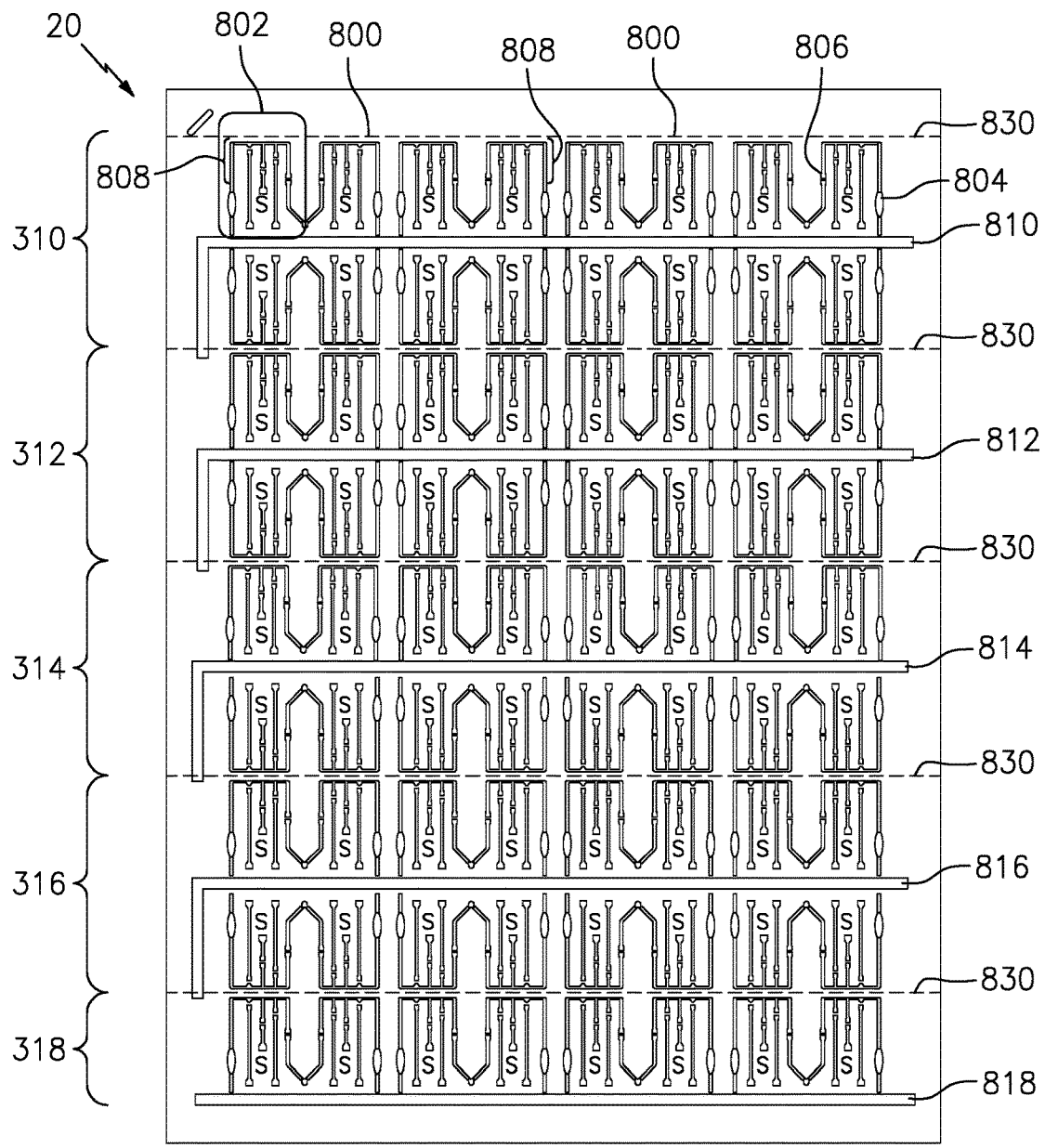
FIG. 8 is a top view of a fluidics layer, in accordance with embodiments of the present disclosure.

In some embodiments, the membrane layer 18 also serves to hold the assay elements (or GNRs) 850 (FIG. 8A) in fixed position in the fluidics channels, where the GNRs have an outer diameter OD larger than the height of the fluidics channel and smaller than the width of the fluidics channel they sit in (i.e., over-width, under-depth open fluidic microchannels). In that case, the membrane 18 elastically deforms around the GNRs 850 and applies a compressive force to the GNRs 850, which permanently fixes the GNRs 850 in the desired position in the desired fluidic channels 800 (FIG. 8). Other embodiments may have slightly undersized width and oversized depth channels relative to the GNRs 850 and, in that case, the channel holds the GNRs 850 in place, as discussed in the aforementioned published patent applications.

Referring to FIG. 8, the fluidics layer 20 is made of a flexible elastomer membrane material, such as PDMS (silicone rubber) or equivalent, similar to the above flexible membrane layer 18, and is permanently covalently bonded to selected regions of the membrane layer 18 to become a single contiguous structure in the selected regions, as discussed herein and in the aforementioned published patent applications.

The fluidics layer 20 provides fluidic channels 800, valve seats 806 and piston chambers 804 for moving fluids (or liquids) to perform the assay. Liquids passed to the fluidics layer 20 from the reservoir layer 14 (thru the other layers 16,18 above), are pumped along fluidic channels 800 by the interaction of piston and valve movement of the membrane layer 18 above with corresponding features in the fluidics layer 20 and the control layer 16.

The fluidics layer 20 has a thickness of about 100 microns; which also is the height of the fluidic channels 800 (discussed hereinafter). The fluidic channels 800 where the GNRs are located 808 have a width of about 125 microns when a tight fit of the GNR in the channel is desired. The non-GNR portions of the channels 800 may have a width of about 250 microns, and the width of the common waste channels 810-818 for each assay strip may be about 1.1 mm to accommodate waste fluid flowing from all the assays connected to that waste channel (e.g., an assay strip). Other thicknesses and dimensions for the fluidic layer 20, and fluidic channel heights and widths, may be used if desired. For example, if the fluidic layer 20 is a "molded" fluidic made from injection molding process (discussed hereinafter), the thickness of the fluidic layer 20 would be much thicker e.g., about 1 mm, as it would have both the channel depth and a bottom thickness below the channels to support the channels, as discussed hereinafter. The fluidic channels 800 are arranged to form fluidic circuits 802 that perform individual assays using an individual sample and detect analyte, as discussed more herein.

The glass slide layer 22 (FIGS. 1,2) gives the fluidic layer 20 structural support and seals the lower side of the fluidic layer channels from the outside providing the bottom of the fluidic channels 800. It also provides an optical "window" for the measurement instrument to view the fluidic channels and to view the assay elements or GNRs and measure the fluorescence therefrom and determine the assay results. The thickness of the glass slide 22 is approximately 210 microns; however, other thicknesses may be used if desired. The glass slide 22 may be made of boro-silicate glass or other materials the provide the function and performance described herein.

Figure 8A:
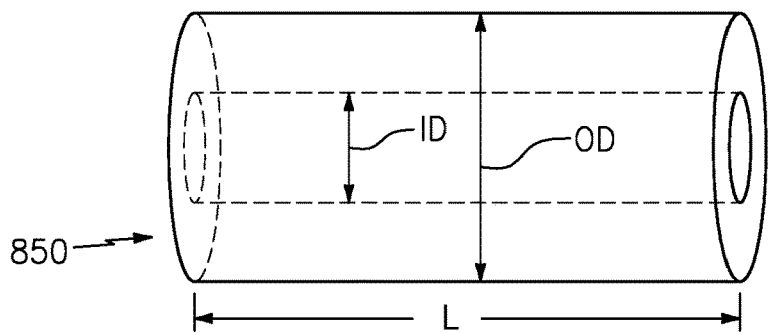
FIG. 8A is a perspective view of an assay element or GNR, in accordance with embodiments of the present disclosure.

Referring to FIGS. 8 and 8A, the fluidics layer 20 moves (or pumps or dispenses) assay fluids (e.g., sample, buffer, detect analyte, and dye), in a predetermined sequence, through a plurality of (e.g., three (3)), functionalized tubular (or cylindrical) transparent flow elements 850 (FIG. 8A) (or assay elements, Glass Nano-Reactors or "GNRs") located at a location 808 in the fluidics channels 800 near the piston 804, to a common waste channels 810-818, and then up the waste towers 410-418 to the common waste reservoir 408 in reservoir layer 14. Each common waste channel 810-818 is used by all the fluidic circuits in the respective assay strip 310-318. The assay strips 310-318 are shown separated by a dashed line 830.

Multiple GNRs 850 in each circuit provide redundancy for the assay and to help validate the results. Other numbers of the GNRs 850 may be used in the fluidic channel for assay measurement if desired. The assay elements 850 or glass nano-reactors (or GNRs) are hollow micro-length tubes made of glass or plastic, similar to that described in the above referenced published patent applications. In particular, the GNR's 850 have a length L of less than 500 microns, e.g., approximately 250 microns, and an inner diameter ID of approximately 75 microns (but may be a small as about 10 microns), and an outer diameter OD of approximately 125 microns. The assay elements are pre-functionalized with an assay capture agent on their interior tubular surface and the outer tubular (or cylindrical) surface is has no measurable capture agent, which may be obtained using processes described in the aforementioned published patent applications. Other dimensions, sizes and geometries may be used for the assay elements 850 provided they meet the functional and performance requirements described herein, or as described in the aforementioned published patent applications listed hereinabove.

The functionalized GNRs 850 (having capture agent on their internal tubular surface) are placed in the open fluidics channels 800 of the fluidics layer 20, are held in position in the open fluidics channels 800 by electrostatic forces, then the fluidics layer 20 is brought into contact with and bonded to portions of the membrane layer 18, thereby sealing the fluidics channels, and holding the GNRs in place. The above assembly may be performed using any desired technique or process, such as that described in the aforementioned published patent applications.

For example, in some embodiments, the covalent bonding technique may involve plasma activation of the PDMS surface prior to contacting the parts or assemblies together. After assembly of the fluidics and membrane layers, in some embodiments, the valves may be actuated (i.e., repeated opening and closing valve for a predetermined time) using pneumatic pressure from the pneumatic channels in a "make and break" process to permanently interrupt covalent bonding of the valve diaphragm with its opposing seat, to prevent the portions of the membrane layer acting as valve diaphragms from bonding to the corresponding opposing valve seat in the fluidics layer, as discussed in the aforementioned published patent applications.

Referring to FIGS. 4A and 4B, the reservoir layer 14 has five (5) adjacent, fluidically-isolated buffer wells (or chambers or reservoirs or banks) 402-406, each bank 402-406 holding the buffer fluid associated with the assay strips 310-318, each strip having a detect analyte (DA) wells, and dye wells. Each of the buffer banks 402-406 may be a locally common fluidically isolated buffer bank (or reservoir or well or chamber) for a respective assay strip 310-318, which supplies buffer fluid to all the individual assays in the respective assay strip. Each sample well 400, DA well 424, and dye well 426 is associated with a separate assay in the assay strips 310-318, and all the assays in a given assay strip are run at the same time.

For example, for each assay within the assay strip 310, the detect analyte (DA) well 424 holds dehydrated detect analyte (DA), and the dye well 426 holds dehydrated dye (e.g., streptavidin), which are each re-hydrated by the buffer liquid from the buffer bank 402-406 as part of performing the assay. As there is only one DA associated with each sample, the cartridge shown herein is a "single-plex" (or single analyte) assay. For the cartridge shown, there are 72 sample wells (corresponding to 72 separate samples), each sample associated with a single detect analyte; thus, it is referred to as a "72×1" cartridge. The sample well size is approximately 50 microliters. The actual sample volume needed from a human or animal specimen (e.g., blood, plasma or serum, spinal fluid, urine, tears, or other type of bodily fluid sample) is 25 microliters, which is diluted by adding an additional 25 microliters of fluid, and fills the sample well. Other sample well sizes and dilution amounts may be used if desired. The assay cartridge of the present disclosure may be used for quantifying antibody concentrations of the desired fluid samples. Other assays may be performed if desired. Also, any number of samples, and corresponding numbers of detect analytes (DA) and dyes may be used if desired, depending on the desired cartridge size.

Referring to FIG. 4B, the layout of the reservoir layer 14 shows two sample wells, two DA wells, and two dye wells grouped together in an oval arrangement (or "pod") 446, which is designed to conserve space in the cartridge 10. Other arrangements, shapes, groupings, and orientations of the wells may be used if desired.

The buffer banks 402-406 are fluidically isolated from each other by buffer walls between each of the banks 402-406, which keep the buffer fluid for a given assay within each "assay strip". For the embodiment shown in FIG. 4A,4B, there are four (4) buffer banks 402-405 that have sixteen (16) sample wells 400 (and corresponding DA 424 and dye 426 wells) and one (1) buffer bank 406 (the last bank) having eight (8) sample wells 400 (and corresponding DA 424 and dye 426 wells). Other numbers of sample wells per local buffer bank may be used if desired (discussed more hereinafter). Other numbers of buffer banks may be used if desired, depending on the desired size of the cartridge and how many samples wells are allocated to a given buffer bank.

Surrounding the outside of the five (5) adjacent buffer banks 402-406 is the common waste reservoir 408, which is common to and fed from all the buffer banks 402-406 and the assay strips 310-318. The common waste reservoir 408 collects waste from each of the assays performed in each of the assay strips 310-318. Having the common waste reservoir 408 allows the cartridge 10 to maximize the number of assay strips, and associated buffer banks, sample wells, and other liquid wells, for a given dimensional footprint and size of the cartridge 10. It only requires one vent hole 322 in the label 12 (FIG. 3) and one vent hole chamber/antechambers 430-434 to minimize the possibility of waste liquid leakage out of the vent hole 322.

To prevent the waste liquid of a given assay strip residing in the common waster reservoir 408 from contaminating or comingling or combining with the other sensitive liquids of other assay strips in the cartridge 10, there 5 pairs (or ten total) cylindrically-shaped towers (or tubes or risers or chimneys or pipes) 410-418 (FIG. 4A,4B), one pair (or two towers) for each of the assay strips 310-318 (for redundancy). A single tower for each assay strip may be used if desired. Waste liquid from each of the assays is dispensed (or pumped) from the fluidic circuits 800 underneath the reservoir layer 14, up through and over the top of the towers 410-418, causing waste liquid to flow out of and over the top of the towers, to run down the outsides of the towers, and to collect in the bottom of the common waste reservoir 408. The height of the towers 410-418 prevents reentry of the waste liquid back into the fluidics circuits of the cartridge, provided the waste liquid level in the common waste reservoir is below the top of the waste towers.

As discussed hereinbefore, there is a pair of waste towers 410-418 for each of the assay strips 310-318 for redundancy purposes, in case one tower becomes clogged, or otherwise becomes non-functional, to avoid a cartridge failure. However, it is not required for functional performance to have a pair of waste towers for each assay strip. The towers should be tall enough to avoid reentry of waste liquid into the top of the tower, but have clearance below the top of the reservoir layer (or bottom of the label) sufficient to not block waste flow out of the towers into the common waste reservoir. For example, the towers may be about 5 mm above the floor of the common waste reservoir 408 (or about 7 mm above the bottom of the reservoir layer) and have about 2 mm of clearance between the top of the waste tower 410 and the top of the reservoir layer 14. Other heights and clearances may be used if desired, provided it meets the functional and performance requirements described herein.

In addition, the pneumatic control lines have a combined star (parallel) and serpentine ("s" like) pattern or layout. This layout avoids having to cross other control channels to reach all the valves and pistons, thereby avoiding the use of "bridges" and the use of additional layers.

Referring to FIGS. 4C, 6, 9,10 and 11, the layout of the pneumatic channels 450 includes a "stub" feature 456, or a parallel segment or branch off of the pneumatic channels 450 used to provide positive and negative pressure to certain regions of the membrane layer 18 to drive the pistons from one longitudinal end of the pistons 804. We have found that running the pneumatic control channels 450 across the center of the pistons 804 causes the piston membrane 18 to collapse into the pneumatic control channel, thereby choking the pressure feed to successive pistons 804 along the same pneumatic control channel. Thus, "stubbing" into one end of the pistons prevents downstream pistons from being choked by upstream pistons themselves. The design connects pneumatic control channels into one end of piston and allows for additional air flow (positive and negative pressure) around the piston port to avoid choking the control channel caused by the flexible membrane collapsing into the pneumatic control channel. Thus, in effect, creating a parallel (or bypass) path for the pneumatic control channel pressure so it is unaffected by piston membrane flexing into the control layer cutout near the stub area 456. The stub approach decouples the pneumatic impedance effects by preventing the membrane 18 from flexing into the pneumatic control channels. In addition, not having the control lines cross-over the fluidic channels at the center of the piston feature (where the fluidic channel is wide), provides a more predictable piston volume by reducing or eliminating piston volume variation caused by the piston membrane being pulled into the pneumatic channel.

Figure 11:
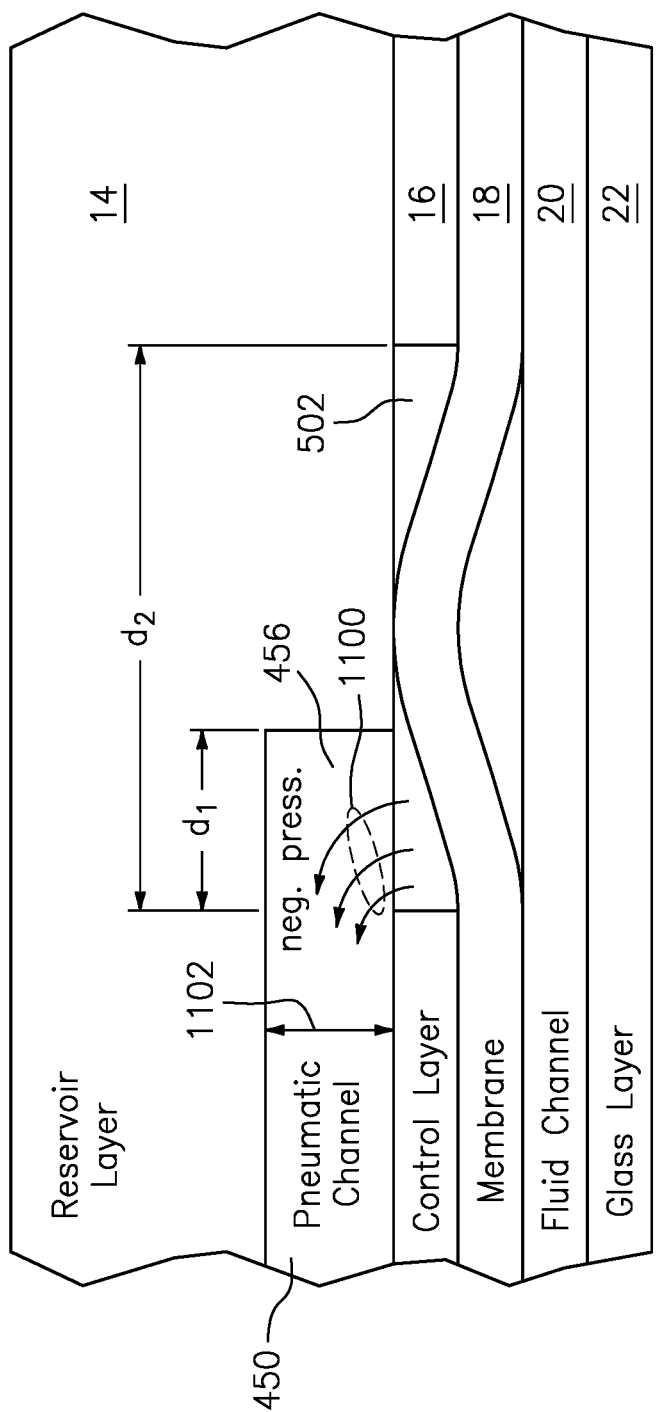
FIG. 11 is a side view of a portion of the assay cartridge showing piston end-drive pneumatic stub, in accordance with embodiments of the present disclosure.

For example, referring to FIGS. 11 and 4D, the stub portion 456 of the pneumatic channel 450 extends a preset distance d1 (e.g., about 0.82) across the length d2 (e.g., about 3.0 mm) of the piston cutout 502 of the control layer 16. When the instrument pulls negative pressure on the channel 450 to actuate the piston membrane, air is removed from the above the membrane layer 18, as shown by the lines 1100. This causes the membrane 18 to lift through the control layer cutout 502 and press against the flat bottom surface of the reservoir layer 14. By having the membrane 18 hit the surface, it creates a consistent repeatable volume movement for the piston. Also, the movement of the membrane 18 does not get pulled into the pneumatic control channel stub area 456 as it is near the end where less membrane 18 deflection occurs. Further, the membrane 18 movement does not affect the pressure flow to the other the pistons down stream.

The pneumatic control lines are about 400 microns wide and 400 microns high. The width and/or height of the pneumatic control channels 450 may be increased to reduce flow impedance if desired, e.g., to about 400 microns wide and 700 microns high. Other dimensions may be used if desired, based on desired pneumatic flow impedance, permitted footprint size, and other factors.

The valves do not exhibit the pneumatic choking effect even though the pneumatic control lines go across the center of the valve cutout, because the control layer cutout for the valves are smaller than they are for the pistons and, thus, the pneumatic pressure does not pull the membrane 18 into the pneumatic control channels.

Figure 9:
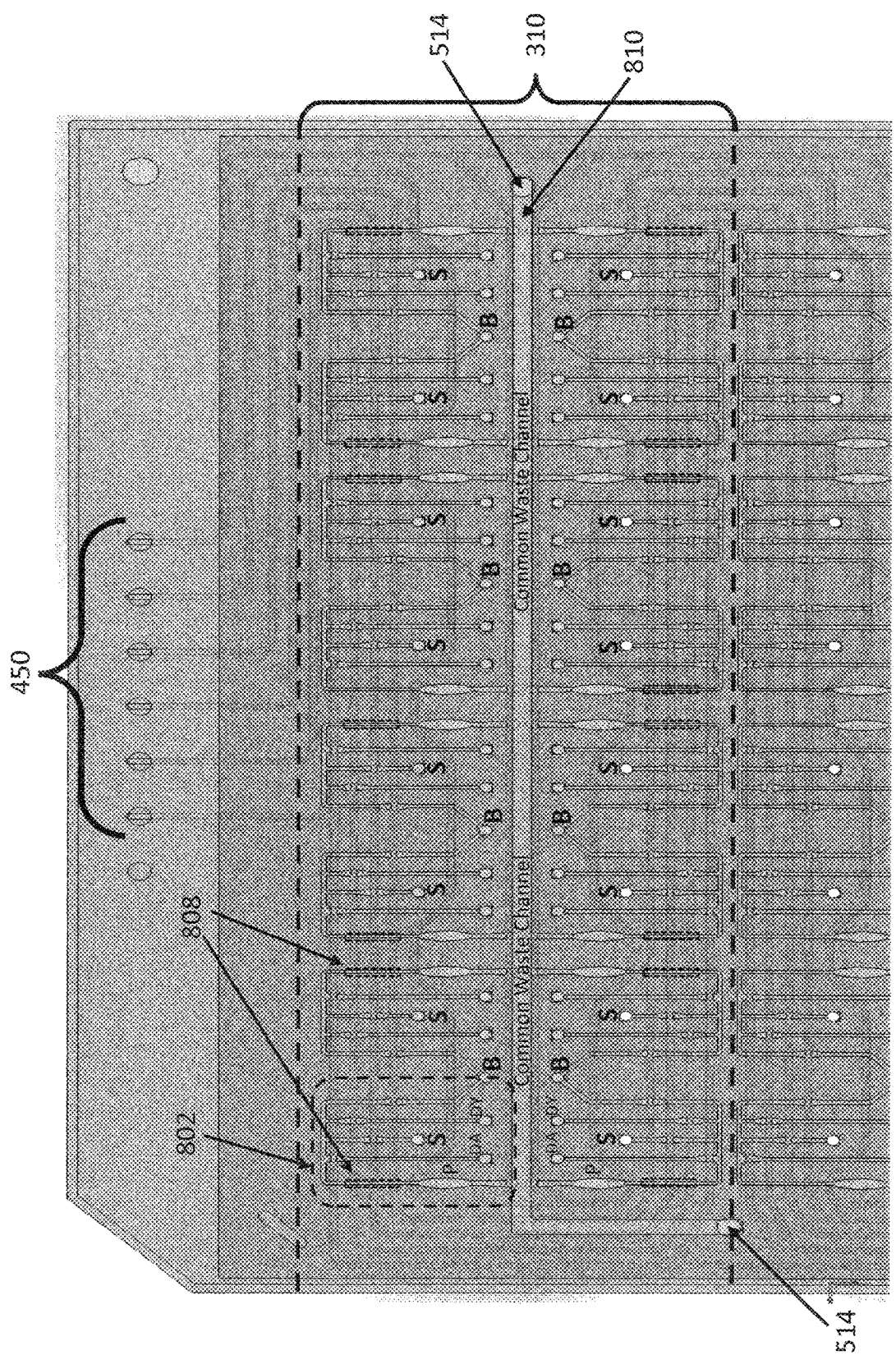
FIG. 9 is a partial top view of a fluidic channels, control elements, and pneumatic lines, in accordance with embodiments of the present disclosure.
Figure 10:
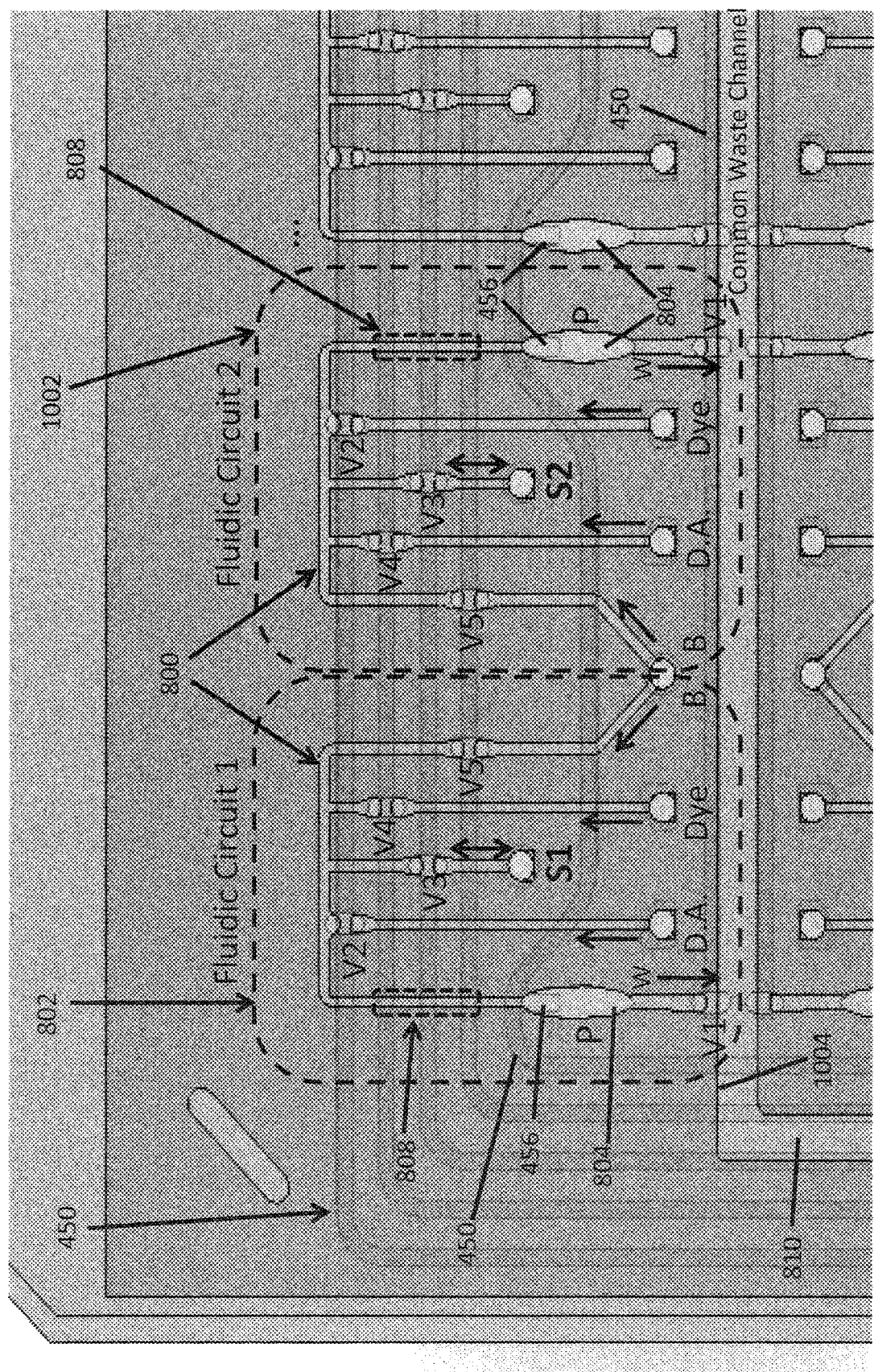
FIG. 10 is an expanded partial view of FIG. 9, in accordance with embodiments of the present disclosure.

Referring to FIGS. 9 and 10, portions of the fluidics layer 20 shown in FIG. 8, are shown in expanded views (as well as the pneumatic control channels shown in the background). FIG. 9 shows the top assay strip 310 of the cartridge with 16 Samples (S) ports and identifies the independent fluidic circuit 802, which includes the fluidics for performing an assay of a single sample S with a single detect analyte (DA), and which is repeated 16 times, one for each Sample/DA assay. The independent fluidic circuit 802 is fluidically isolated from all the other fluidic circuits on the cartridge 10 and is used to perform measurements in parallel on different samples S. Also, each fluidic circuit 802 is functionally and architecturally identical; but, certain circuits may be oriented as mirror images of other circuits to provide the overall functionality and footprint desired. Since the fluidic circuits 802 are identical copies, the pneumatic control lines (or channels) 450 may be shared across all the fluidic circuits and thereby use a small set of independently controlled pneumatic channels 450, limiting the complexity of the instrument that controls the cartridge 10.

Referring to FIG. 10, for example, the cartridge 10 with 72 samples each measuring a separate detect analyte DA, may have as few as 6 pneumatic channels 450, where each of the pneumatic channels 450 connects the same set of functional features located in each of the independent fluidic circuits, such as a set of Sample valves V3 that allow the sample for each circuit to flow at a particular time, a set of Detect Analyte (DA) valves V2 that allow the Detect Analyte for each circuit to flow at a particular time, a set of Waste valves V1 at the output of a set of Pistons P 804 which allow assay fluids to flow to the common waste channel 810, a set of Buffer valves V5 that allow the Buffer liquid to flow at a particular time, and the set of Pistons P which actuate the Pistons at a particular time. Each of these sets of functionality are connected to each other through a single contiguous pneumatic channel 450 (using non-overlapping serpentine and parallel channel patterns) which terminates at one end at a pneumatic interface with pneumatic ports which connects to the pneumatic ports on the instrument (as discussed herein), and at the other end at the last feature in the string of connected features (as also discussed herein with FIGS. 4A, 4B and 4C).

Referring to FIGS. 9 and 10, it also shows the Buffer (B) port and indicates that the buffer ports in each assay strip are fed from a common buffer bank or well (as discussed herein with for the reservoir layer, FIGS. 4A,4B). In some embodiments of the present disclosure, every two adjacent fluidic circuits share a common Buffer port (B) to save space. Alternatively, each fluidic circuit may have its own buffer port (B) if desired. In either case, each of the fluidic circuits 802 are still fluidically isolated from each other. It also shows how each of the fluidic circuits 802 is connected to the common waste channel 810, and that on each end of the common waste channel 810 is a port 514 that connects to the waste towers 410. It also shows selected ports for the Detect Analyte (DA) and the Dye (DY) and a select piston (P) and assay elements (GNRs) location, more details of which are shown in FIG. 10.

Referring to FIG. 10, a further enlarged view of FIG. 9 is shown, which shows the details of two fluidic circuits 802,1002, including 5 valves (V1-V5), a piston (P), and Sample input port (S), which is fluidically connected to a sample well, a Detect Analyte input port (DA), which is fluidically connected to the DA well, a Dye input port (Dye), which is fluidically connected to the Dye well, and a Buffer input port (B) which is fluidically connected to the locally common Buffer bank 402-406 for this assay strip, each described hereinbefore with the reservoir layer (FIGS. 4A,4B). In addition, the location 808 of the assay elements (or GNRs) 850 (FIG. 8A) are shown in the same channel as the piston (P). The arrows show the direction of fluid flow, e.g., from the fluid input ports (B, S, DA, Dye) into the particular arm of the fluidic circuit. The piston (P) works with the corresponding valves (V1-V5) to create a microfluidic pump to move the assay fluids along the desired flow path, described further below. At various points during the assay, the waste valve V1 opens and allows the waste liquid (W) to flow into the common waste channel 810. When the common waste channel 810 (in the fluidics layer) becomes full, it pushes (or pumps) the waste liquid up the waste towers 410-418 and into the common waste reservoir 408 (in the reservoir layer) described hereinbefore.

For a given assay strip, the corresponding valves and pistons for each of the fluidic circuits are actuated together and operate in unison. For assay strips that are not being used, the valves and pistons associated therewith are still actuated; but, as there is no sample or buffer fluid loaded into that assay strip, they operate dry and do not produce any results (and do not use up any analyte or dye and thus are still available for use).

As sample assay protocol is shown below (for an ELISA assay):
1. Prime (or fill) the cartridge with Buffer
2. Backfill the SA-Dye and Detect Antibody reagent reservoirs from the Buffer (SA=Streptavidin)
3. Run the Sample (e.g., move Sample through GNR channel, back and forth)
4. Flush the Sample (e.g., move Buffer through GNR channel to Waste)
5. Run the Detect Antibody (e.g., move Detect Antibody through GNR channel, and let is soak for a preset time)
6. Flush the Detect Antibody (e.g., move Buffer through GNR channel to Waste)
7. Run the SA-Dye (e.g., move Dye through GNR channel, back and forth)
8. Concurrent with running the Dye, run the 'Find Channels' scan routine to locate the channels in preparation for GNR measure scanning
9. Flush the SA-Dye (e.g., move Buffer through GNR channel to Waste)
10. Run Measure Scan Each pump step above is a combination of valves (V1-V5) and piston (P) states that are run in a loop to create the desired fluid flow. A simplified example of a single pump cycle of pumping 'Buffer' fluid to the common 'Waste' channel would be as shown in the below table:

| Buffer Valve (V5) | Piston (P) | Waste Valve (V1) | Sample Valve (V3) |
| --- | --- | --- | --- |
| Open | Close | Close | Close |
| Open | Open | Close | Close |
| Close | Open | Close | Close |
| Close | Open | Open | Close |
| Close | Close | Open | Close |
| Close | Close | Close | Close |

Pumping any other reagent or fluid in the cartridge would be essentially the same cyclical process except different valves would be used. For example, for the controller to pump the 'Sample' fluid S to the common 'waste' channel it would open the 'Sample' valves (V3) at the same step in the above process where it had opened the 'Buffer' valves (V5) and keep the 'Buffer' valves (V5) closed, such as is shown in the below table.

| Buffer Valve (V5) | Piston (P) | Waste Valve (V1) | Sample Valve (V3) |
| --- | --- | --- | --- |
| Close | Close | Close | Open |
| Close | Open | Close | Open |
| Close | Open | Close | Close |
| Close | Open | Open | Close |
| Close | Close | Open | Close |
| Close | Close | Close | Close |

A similar change would be made for moving fluids from DA to waste and from Dye to waste. In the case of a "back-and-forth" fluid motion, the valves would stay fixed in the desired position and the piston (P) would open and close to move the fluid back-and-forth along the same channel paths.

Referring to FIGS. 8, 9 and 10, we have also found that any fluidic channel wall (with the proper orientation to the channel) may be used for one side of a valve seat. In particular, the waste valve (V1, FIG. 10) for each of the fluidics circuits associated with a given common waste channel (and assay strip) use a portion of the common waste channel wall as one side of the valve seat. Using the channel wall as one side of the valve seat allows the fluidic circuit footprint to be smaller, in particular it allows the buffer banks to be vertically narrower. Otherwise, a portion of the fluidics channel in which the valve is located would need to be formed (off of the common waste channel) and then form the valve seat, as is shown for the other valves (V2-V5) in the fluidics circuit, which would require more space, and thus a larger footprint. This may be done using injected molded channels or knife cut channels, or other techniques that provide precise square edges for the fluidic channels.

More specifically, in some embodiments, the fluidic layer 20 may be made by knife-cutting a sheet made of PDMS (or silicone) to form the side walls of the fluidic channels 800 and the valve 806 and piston 804 features. In that process, a machine-driven knife is used to precisely cut the PDMS through the entire thickness, about 100 microns (0.1 mm), of the PDMS sheet and then the loose residual strips of PDMS are removed from the cut sheet (e.g., with tweezers or a vacuum or other removal technique) to form the channels and features. The knife-cut PDMS layer (or template) 20 is disposed on or attached to the glass slide layer 22 to form the bottom surface of the fluidic channels, valves and pistons, as shown in FIGS. 1 and 2.

We have found that the fluidics layer 20 may be made using a precision injection molding process where optically clear liquid PDMS (or silicone), e.g., liquid silicone part no. MS-1002 made by Dow Corning, is injected into a mold having the fluidic channels and features in the mold template. The process is performed at the appropriate temperature, pressure, and cure time, to obtain the desired results. The resulting fluidics layer 20 (or "molded" fluidics layer), may have a thickness of about 1.1 mm, having the fluidic channels and features (e.g., valves and pistons) molded into the upper surface of the layer 20, e.g., about 0.1 mm (or 100 microns). Other thicknesses may be used if desired.

To ensure the dimensions of the final "molded" fluidics layer 20 has the tolerances desired for the fluidic channels 800, we have also found that the layer 20 should be placed on a non-stick surface, such as surface coated PTFE, e.g., Teflon® or the like, during the curing process, after removal from the injection mold, as the PDMS material continues to out-gas and shrink in size as it cures.

Also, because the molded fluidic layer 20 is a flexible material, a relatively (or substantially) rigid backing surface, such as polycarbonate plastic having a thickness of about 100-200 microns, is or disposed on (or placed on or attached to) the layer 20 to allow for precise alignment layer 20 with the rest of the cartridge 10. Other materials and thicknesses may be used if desired provided it provides the function and performance described herein. Before attaching the layer 20 to the flexible membrane layer 18 and the rest of the cartridge 10, the GNRs (or flow elements) are inserted into the fluidic channels of the fluidics layer 20, e.g., by a pick-and-place process, such as is described in the aforementioned commonly-owned published patent applications. The rigid backing may be a removable backing, if desired, which can be removed after assembly of the cartridge 10. If the rigid backing is not removed, it should be made of a material that is transparent to the wavelengths of light used by the instrument, to permit the instrument to perform the assay and read the assay results.

Using an injection molding process to manufacture the fluidics layer 20 simplifies the manufacturing process by eliminating steps and parts. In particular, it eliminates the need to perform knife-cutting of the PDMS, and the associated removal of the residual knife-cut strips of PDMS and the inspection process to ensure the residual PDMS strips are all removed. Also, it eliminates the need for the glass slide layer 22, and the assembly step of binding the glass slide layer 22 to the fluidics layer 20, and the step of cleaning the bottom of the glass slide after assembly. Thus, using such a injection molded process to make the "molded" fluidics layer 20 increases manufacturing through-put by reducing the time to fabricate each portion and the assembly steps. Further, it is less expensive to produce than the knife-cutting process described above and provides improved dimensional repeatability.

Using a "molded" fluidic layer also reduces a risk of delamination of the glass layer 22 (or other rigid layer) from the rest of the cartridge. As the reservoir layer 14 is made of rigid plastic and is not always perfectly flat across its entire lower surface, which can cause delamination of the fluidic layer from the glass layer 22, which is relatively rigid and resists bending. The bottom surface of reservoir layer 14 may be "planed" with a planing machine (or the like) to ensure the surface is flat, but this requires an additional process step. The molded fluidic layer 20 is flexible and, thus, does not require a flat mating surface, allowing for more tolerance on the flatness of the bottom surface of the reservoir layer 14.

Another advantage of molded fluidics layer 20 is the width of the fluidic channels may be made narrower, e.g., from about 250 microns for the fluidic layer made by knife-cutting to about 125 microns or less for the "molded" fluidic layer 20, permitting tight or snug fitting of the GNR elements in the fluidic channels. Also, the separation between adjacent fluidic channels may be made smaller, e.g., from about 1.5-2.0 mm separation for the fluidic layer made by knife-cutting, down to about 200 microns separation between channels for the "molded" fluidic layer 20. This reduction in space may be used to decrease the footprint of the cartridge 10 or increase the capacity (e.g., number of fluidic channels or circuits) of the cartridge 10 for the same size footprint.

A further advantage of the molded fluidics layer 20 is that one can design 3D features into the fluidics layer, having various depths and geometries, as desired. In particular, the pistons may be made deeper or shallower than the rest of the fluidics channel, and may be made to have a geometry other than a flat bottom and flat sides, such as rounded bottom and/or sides, spherical shape, or other 3D geometry. Also, the geometry and height of the valve seats may be designed as desired, such as oval, rounded, square, flat-top triangle, reduced height below the top of the channel, or etc. Also, similar to the pistons, the rest of the fluid channel walls and floor may be structured with a geometry other than flat, such as rounded, bottom and/or sides, spherical shape, or other 3D geometry. Also, the fluidic channel may have a varying depth, such as a varying or slanted bottom or channel width, to create the desired flow effects, such as a channel-type filter having a slanted bottom and/or side walls, to trap different sized particles or cells. Any other 2D or 3D geometry may be used if desired to create the desired effect within the fluidic channels.

It should be understood that the "molded" fluidic process may be used to manufacture the fluidic layer of the assay cartridge described in the aforementioned commonly-owned published patent applications, with similar corresponding changes being made (e.g., elimination of the bottom glass slide layer and use of a bottom supporting layer), and providing similar features and advantages as discussed above.

Figure 12:
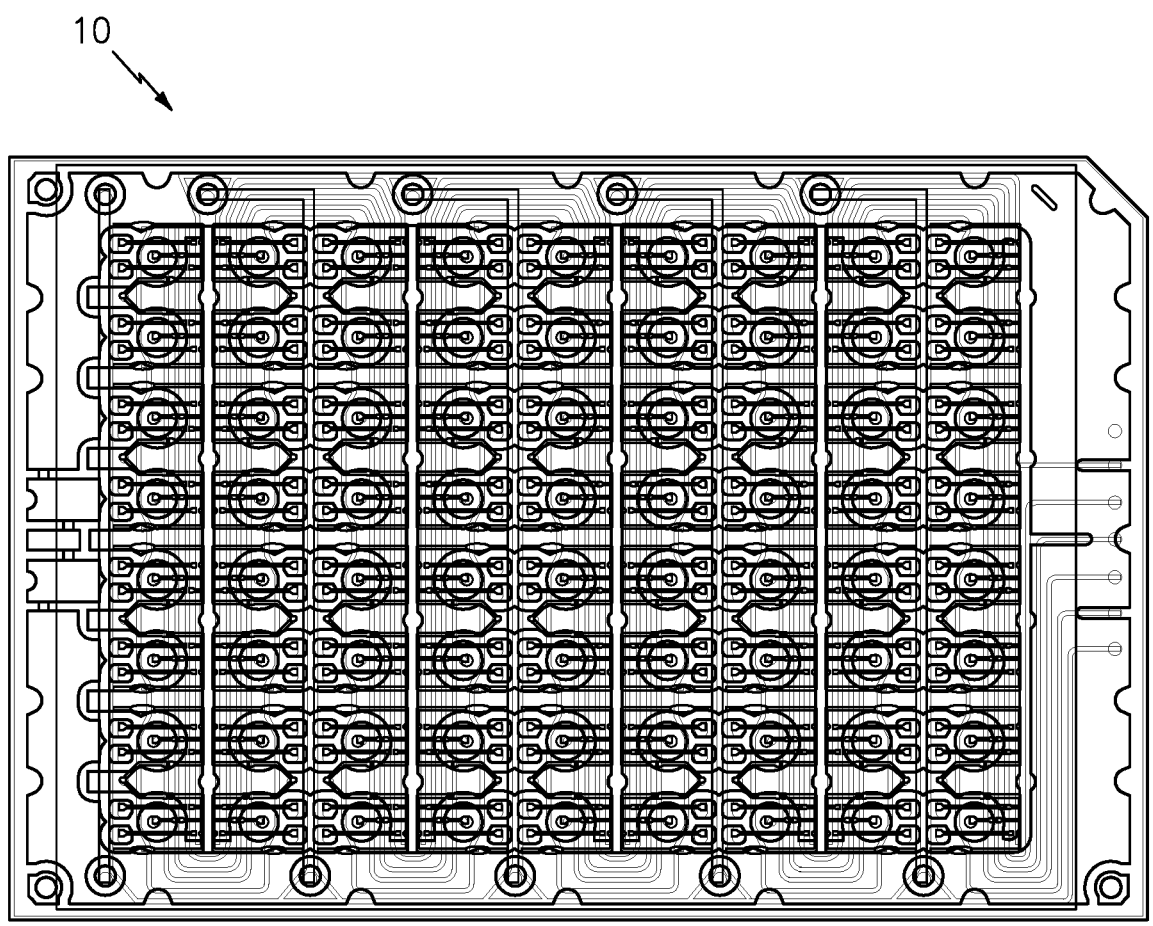
FIG. 12 is a top view of the assay cartridge, in accordance with embodiments of the present disclosure.
Figure 13:
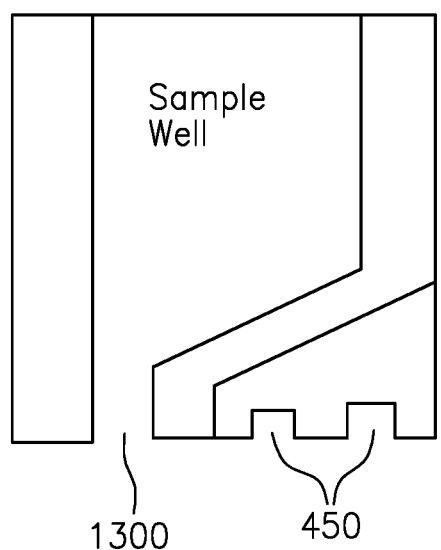
FIG. 13 is a partial side cut-away view of a sample well and pneumatic channels, in accordance with embodiments of the present disclosure.

Referring to FIGS. 12 and 13, a top view of an embodiment of the cartridge assembly 10 of the present disclosure is shown, showing the fluidics layer 20 and the reservoirs, as well as the pneumatic channels 450 and the through-holes (vias). FIG. 13 illustrates how the various reservoirs in the reservoir layer interact with the fluidics ports, channels, and circuits. For certain types of precise manufacturing processes, such as injection molding, it is possible to have pneumatic channels be tightly packed with the reservoirs or wells. For example, the Sample well exit hole (or via) 1300 on the bottom of the reservoir layer 14 can be offset from the center of the well allowing one or more pneumatic channels to cut across the well at the bottom of the layer and not affect the sample well, as shown in top view in FIG. 12, and also shown in an example side view in FIG. 13. This technique may also be used for the dye and detect analyte wells.

Figure 14:
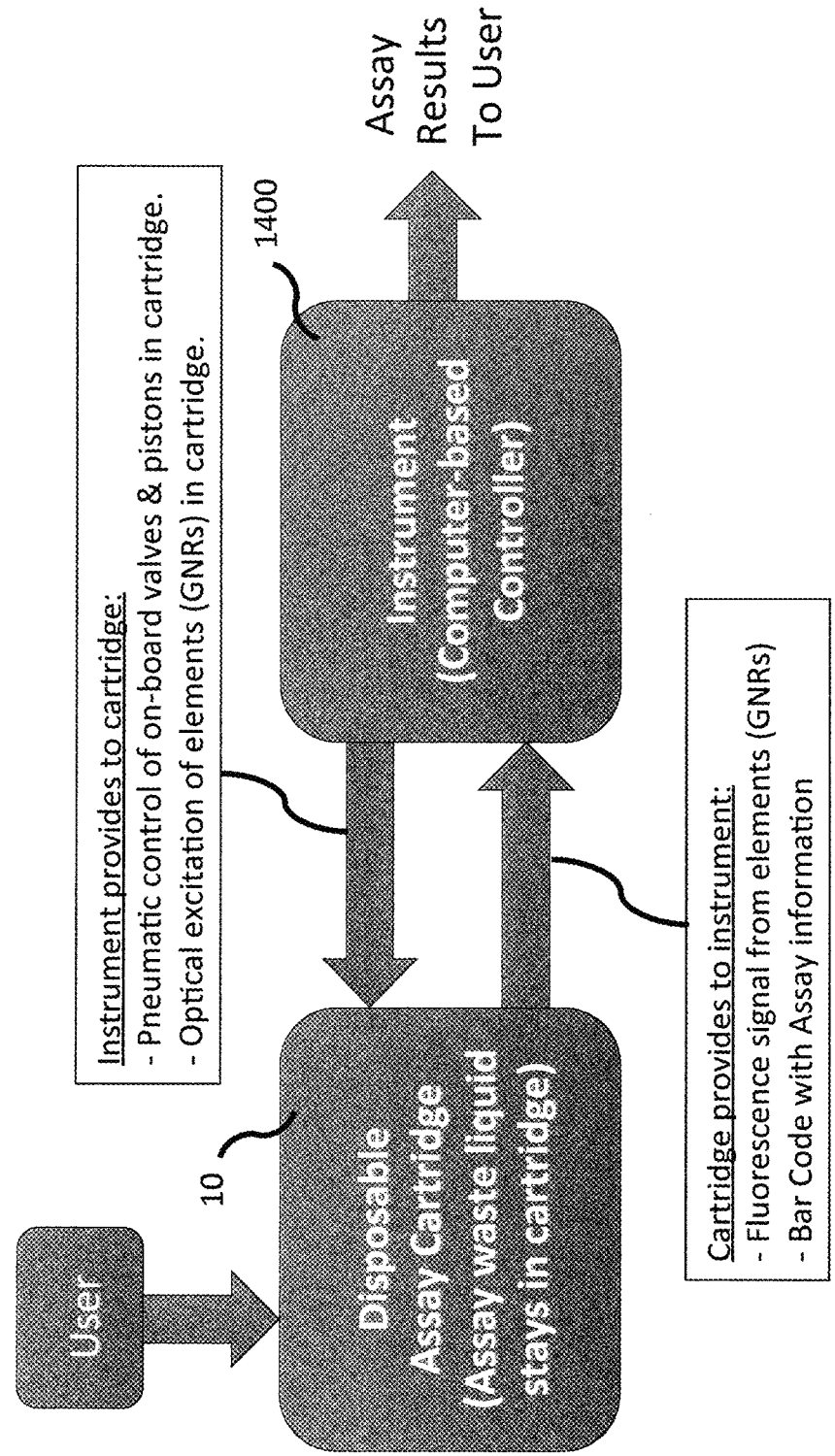
FIG. 14 is a block diagram of the assay cartridge and the optical instrument, in accordance with embodiments of the present disclosure.

Referring to FIG. 14, a block diagram of the assay cartridge 10 and the instrument 1400 is shown. The instrument may be similar to that shown and described in the aforementioned commonly-owned published patent applications 2015/0086424 A1, 2015/0087558 A1, 2015/0083320 A1, 2015/0083313 A1, 2014/0377146 A1, 2014/0377852 A1, 2015/0087544 A1, 2015/0087559 A1. To perform the assay, the user loads the disposable assay cartridge 10 described herein into the instrument 1400, and may also load the bar code information into the instrument 1400 via a bar code reader or the like. The user then pipettes (or otherwise injects) the sample and buffer liquids into the cartridge 10 for the desired assay strip being run, e.g., 16 samples. The user then closes the instrument cover and presses a "GO" button on the instrument 1400, and the instrument 1400 runs the assay and obtains the results. The instrument 1400 provides pneumatic control of the valves and pistons in the cartridge 10 (as described herein) and optical excitation of the assay elements (GNRs) 850 (FIG. 8A) in the cartridge 10. The cartridge 10 provides a fluorescent optical signal from the assay flow elements, which is read by the instrument 1400. The instrument 1400 locates the fluidic channels and the GNRs 850 and optically scans the GNRs 850 and measures the fluorescence and provides the assay results to the user.

Figure 15:
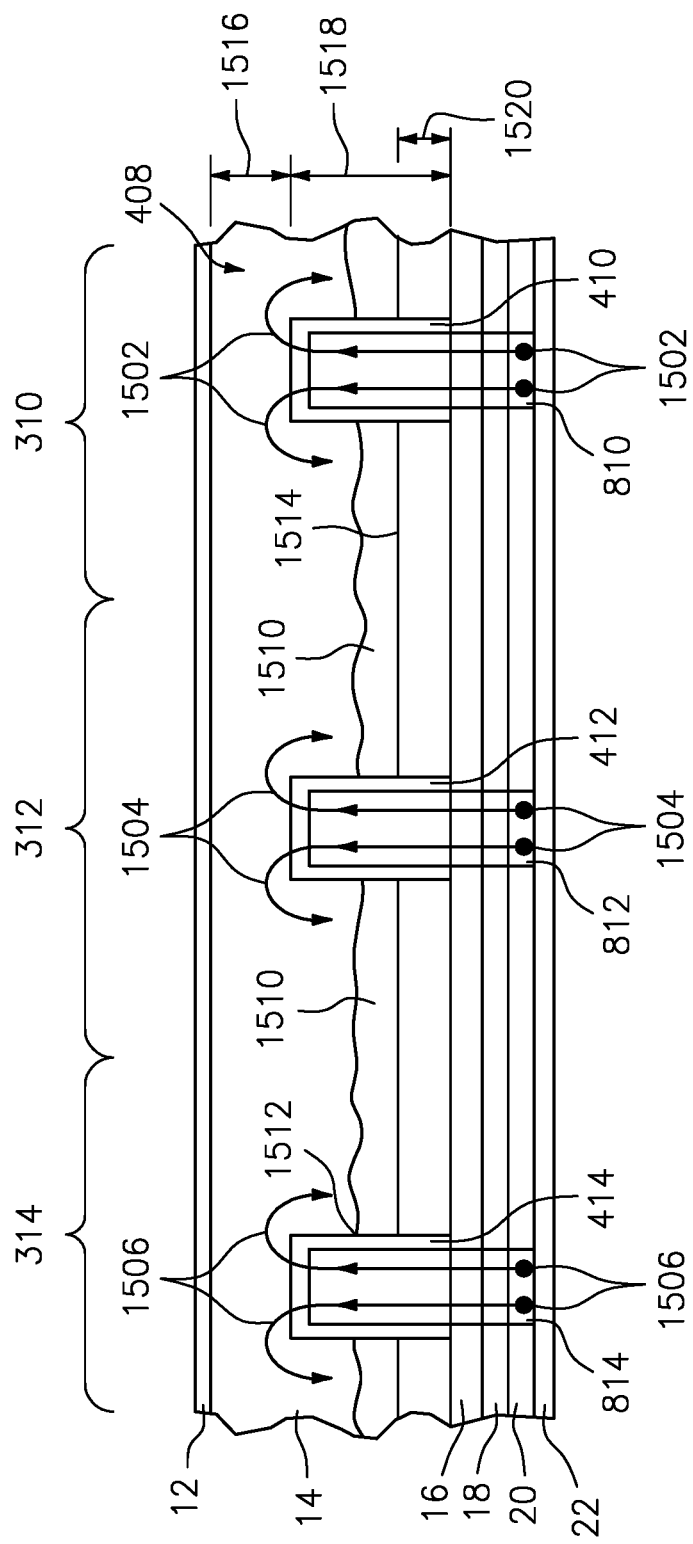
FIG. 15 is a partial side cut-away view showing example operation of three waste towers, in accordance with embodiments of the present disclosure.

Referring to FIG. 15, an example of operation for three assay strips 310-314, and single towers 410-414 for each strip is shown. It shows an exaggerated view of the lower layers 16-22 and how waste liquid 1502-1506 flows from the common waste channel 810 of the fluidic layer 20, up the waste towers 410-414, over the top of the towers 410-414 and into the common waste reservoir 408. It also shows how the separate assay strips 310-314 would operate to pump their respective waste liquid 1502-1506 into the common waste reservoir 408 where they would comingle (or combine) as common waste liquid 1510 and the level 1512 of the waste liquid 1510 would be below the height of the towers 410-414, and thus provide waste liquid isolation between the assay strips 310-314.

Approximate dimensions of the waste towers 410-418 may be: height of about 7 mm (from bottom of reservoir layer 14 to top of tower shown as numeral 1518), outer diameter of about 4.17 mm, which may taper out to about 4.48 mm at the bottom, inner diameter of 1.36 mm, which may taper out to about 1.83 mm at the top of the tower. Tapering of the tower dimensions may be done to permit injection molded manufacturing to enable removal from the part from the mold. Alternatively, the towers may have a constant inner and outer diameter with no taper if desired, e.g., if the part is machined or not molded. Also, the approximate clearance (numeral 1516) between the top of the towers and the top of the reservoir layer 14 (or bottom of the label 12) is about 2 mm, and the distance (numeral 1520) from the bottom of the reservoir layer 14 and the bottom 1514 of the common waste reservoir 408 is about 2 mm, as is shown in FIG. 15. Other clearances may be used if desired; for example, to further reduce the risk of waste flowing back down the towers, the towers may be taller, e.g., about 8.0 mm, making the top of the towers closer to the top of the reservoir layer, leaving the clearance at about 1.0 mm. Other shapes, sizes and dimensions of the waste towers 410-418 may be used if desired, provided it provides the functions described herein.

In addition, the waste towers 410 should not be of such a size and shape as to create back pressure and/or liquid head pressure that would prohibit the pistons from pumping the waste up the towers and into the common waste reservoir. Also, additional or alternative techniques may be used to reduce the possibility of waste liquid reentry into the towers (and thus the fluidics layer of other strips), such as vented caps, one-way moving covers or lids, reverse flow inhibitor flanges or wings, check valves, and the like.

Figure 16:
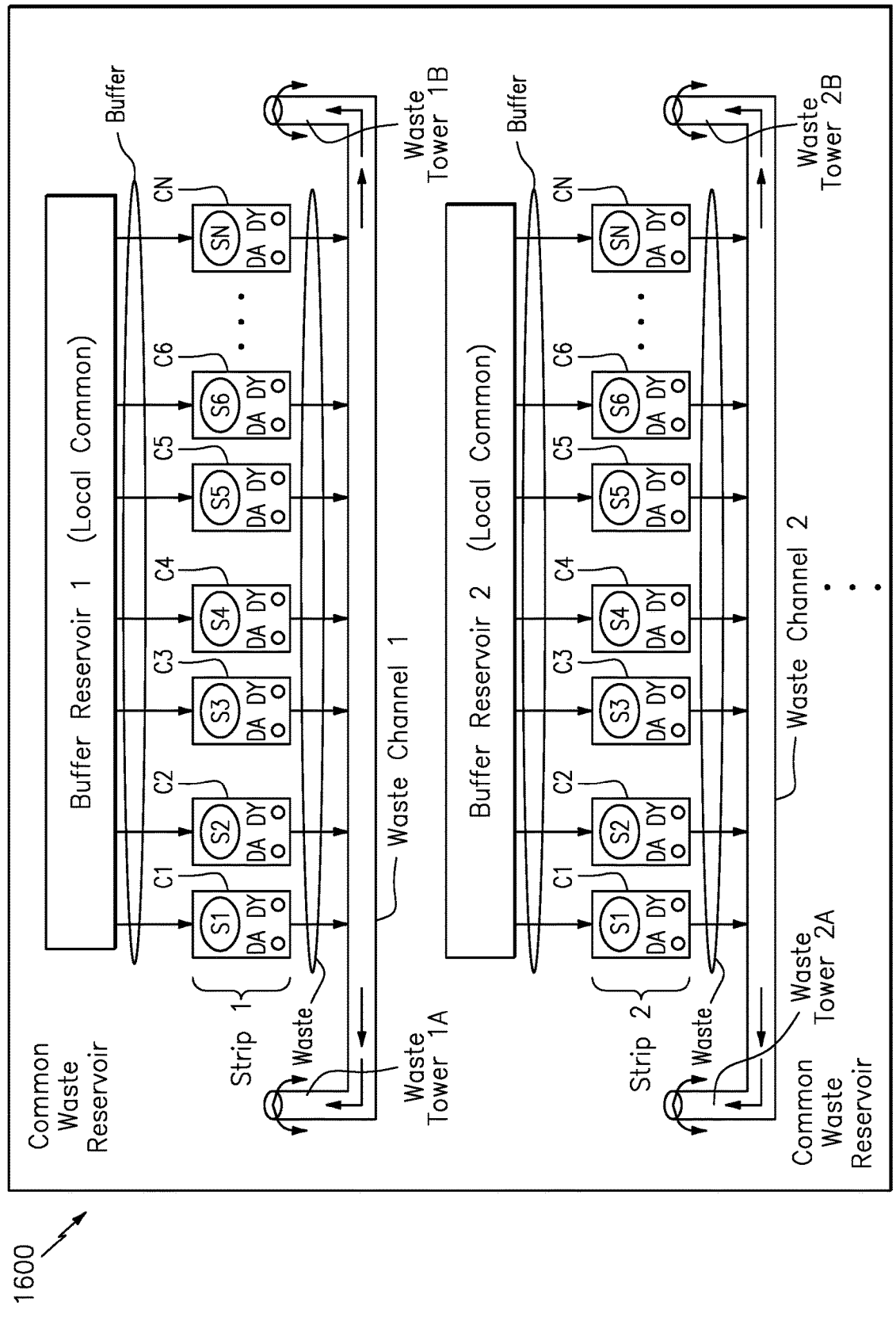
FIG. 16 is a generalized block diagram showing two generalized assay strips, in accordance with embodiments of the present disclosure.

Referring to FIG. 16, a generalized block diagram 1600 of one embodiment of the present disclosure is shown with two generalized assay strips (Strip 1 and Strip 2). For each assay strip, there are a plurality of fluidic circuits C1-CN, each circuit having a corresponding sample well S1-SN, and a corresponding Detect Analyte (DA) and Dye (DY). For Strip 1, the fluidic circuits each receive their buffer liquid from a locally common Buffer Reservoir 1, and each of the fluidic circuits dumps is waste liquid to a locally common waste channel 1. Waste channel 1 is connected to redundant waste towers 1A and 1B, which dump into a common waste reservoir, similar to that discussed herein before.

Similarly, for Strip 2, the fluidic circuits each receives their buffer liquid from a locally common Buffer Reservoir 2, and each of the fluidic circuits dumps is waste liquid to a locally common waste channel 2. Waste channel 1 is connected to redundant waste towers 2A and 2B, which dump into a common waste reservoir, similar to that discussed herein before. Also, Buffer Reservoir 1 is fluidically isolated from Buffer Reservoir 2, and waste channel 1 is fluidically isolated from waste channel 2. A similar arrangement exists for assay Strips 3, 4 and 5 in the cartridge. Thus, the each assay strip on the cartridge is completely separate or segmented from each other assay strip on the cartridge.

Accordingly, embodiments of the present disclosure may have a set of circuits that each use a locally common but fluidically isolated buffer reservoir (or bank) and that dispense into a locally common but fluidically isolated waste channel, and that the waste channels dispense their waste liquid into a common waste reservoir via towers or an equivalent flow feature that prevents liquid from entering the fluidics layer or circuits of the unused assay strips, or other unidirectional flow feature/device/component.

Figure 17:
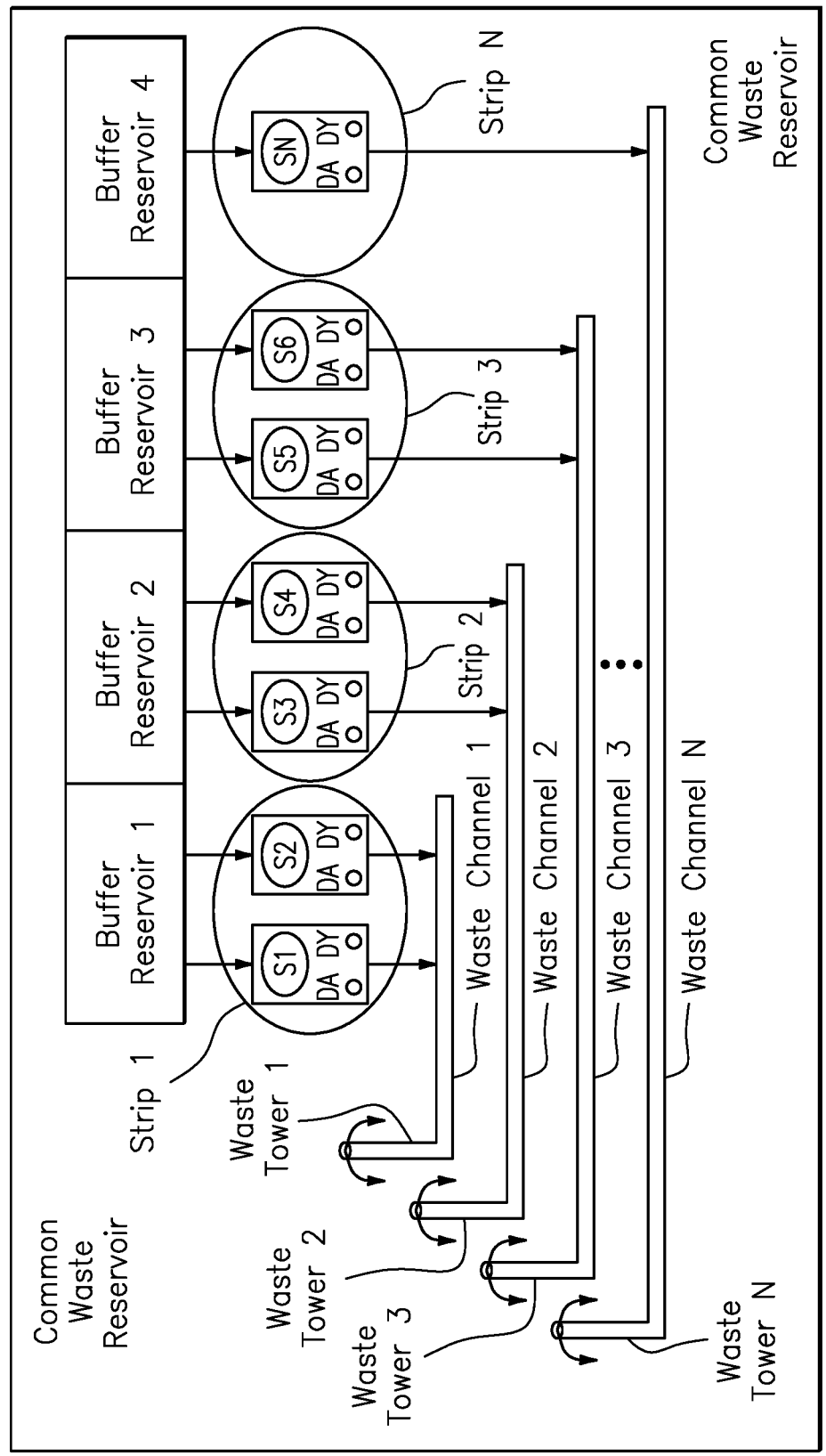
FIG. 17 is a generalized block diagram showing N generalized assay strips, in accordance with embodiments of the present disclosure.

Referring to FIG. 17, another generalized block diagram 1700 of one embodiment of the present disclosure is shown with N generalized assay strips (Strip 1-Strip N). For each assay strip, there are a plurality of unique fluidic circuits C1-C2, C3-C4, C5-C6, CN, each circuit having a corresponding unique sample well S1-S2, S3-S4, S5-S6, SN, and a corresponding Detect Analyte (DA) and Dye (DY). For Strip 1, the fluidic circuits each receives their buffer liquid from a locally common fluidically isolated Buffer Reservoir 1, and each of the fluidic circuits dumps is waste liquid to a locally common fluidically isolated waste channel 1 which is connected to waste tower 1, which dumps into a common waste reservoir, similar to that discussed hereinbefore. For Strip 2, the fluidic circuits each receives their buffer liquid from a locally common fluidically isolated Buffer Reservoir 2, and each of the fluidic circuits dumps is waste liquid to a locally common fluidically isolated waste channel 2 which is connected to waste tower 2, which dumps into a common waste reservoir, similar to that discussed hereinbefore. This can repeat for N strips as shown in FIG. 17 and all of the waste will be isolated in the common waste reservoir, provided the functional requirements for the towers described herein are met. If desired, Buffer Reservoir 1 could be split into two buffer reservoirs one for each of the circuits C1,C2, as indicated by the line 1700.

Accordingly, an assay strip may, in some embodiments, be a single sample or single circuit, provided the single circuit has its own dedicated waste channel feeding a waste tower and being supplied by its own dedicated fluidically isolated buffer reservoir and the common waste reservoir would not comingle the liquids.

Figure 18:
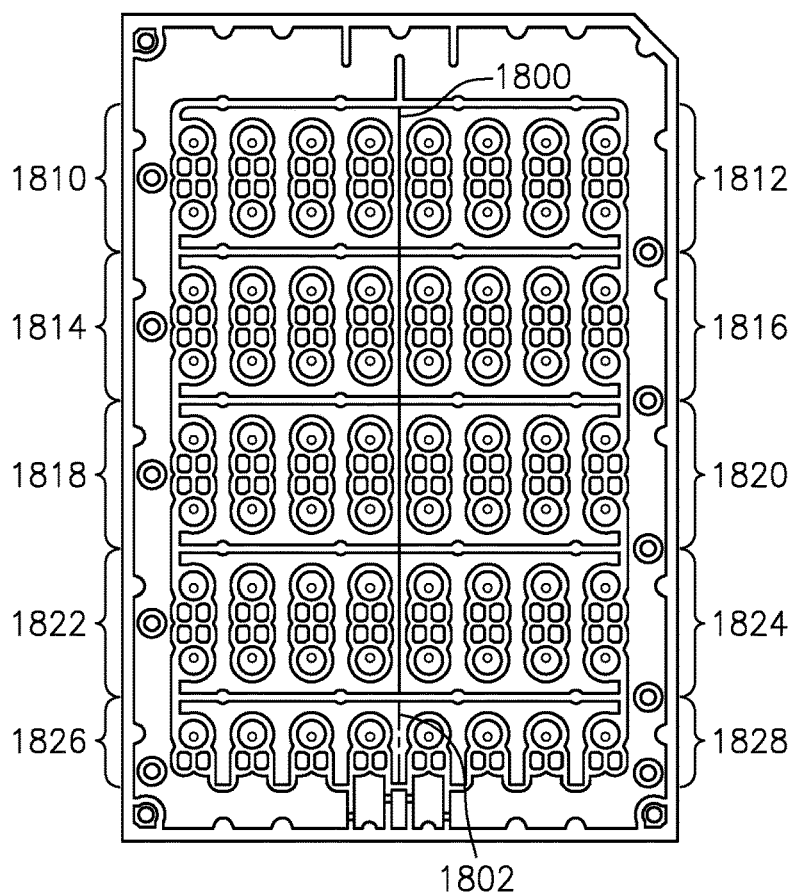
FIG. 18 is a top view of a reservoir layer of an alternative embodiment, in accordance with embodiments of the present disclosure.
Figure 18A:
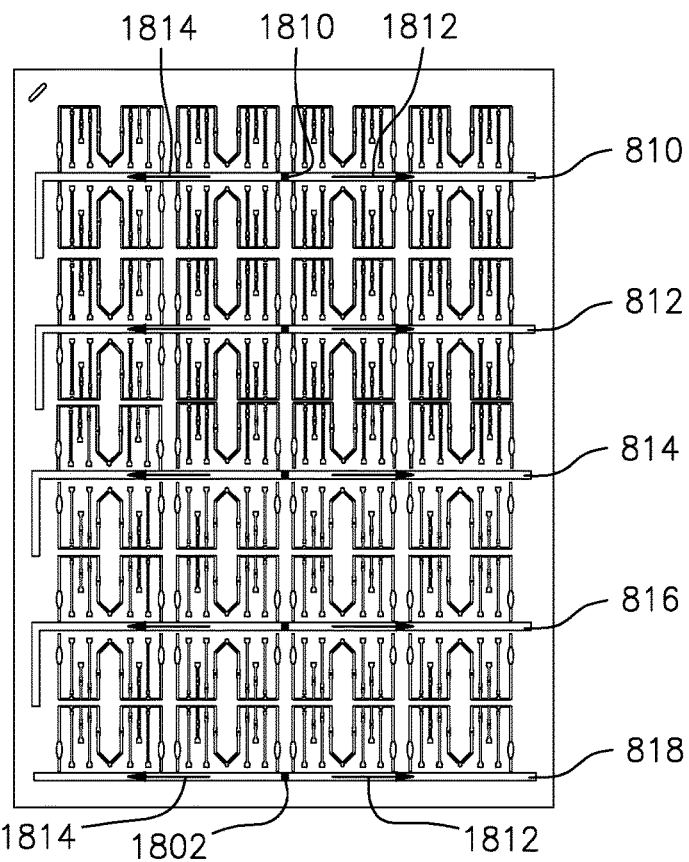
FIG. 18A is a top view of a fluidics layer of the alternative embodiment of FIG. 18, in accordance with embodiments of the present disclosure.

Referring to FIGS. 18 and 18A, the cartridge discussed herein with 5 assay strips may be modified to have 9 assay strips 1810-1826 or 10 assay strips or 1810-1828, by splitting the buffer banks in half vertically as shown by a line 1800 and splitting each of the common waste channels 810-818 in half to create two waste channels as indicated by a vertical line 1810, one on the left side and one on the right side. Each side connects to its own tower, and the waste flow would be as shown by lines 1812, 1814. In that case, the 16×1 assay strips described hereinbefore would become 8×1 assay strips 1810-1824. The last assay strip 1826 would not need to be split as it is already an 8×1 strip. However, if desired, to create two 4×1 assay strips, the last buffer bank 406 and last common waste channel 818 could be split as shown by lines 1802. If that is done, then there would be 10 assay strips, with the last two assay strips 1826,1828 being 4×1. While this configuration removes the redundancy of having two towers for each assay strip shown in other embodiments, there would still be no comingling of waste from the common waste reservoir to any other assay strip.

Figure 19:
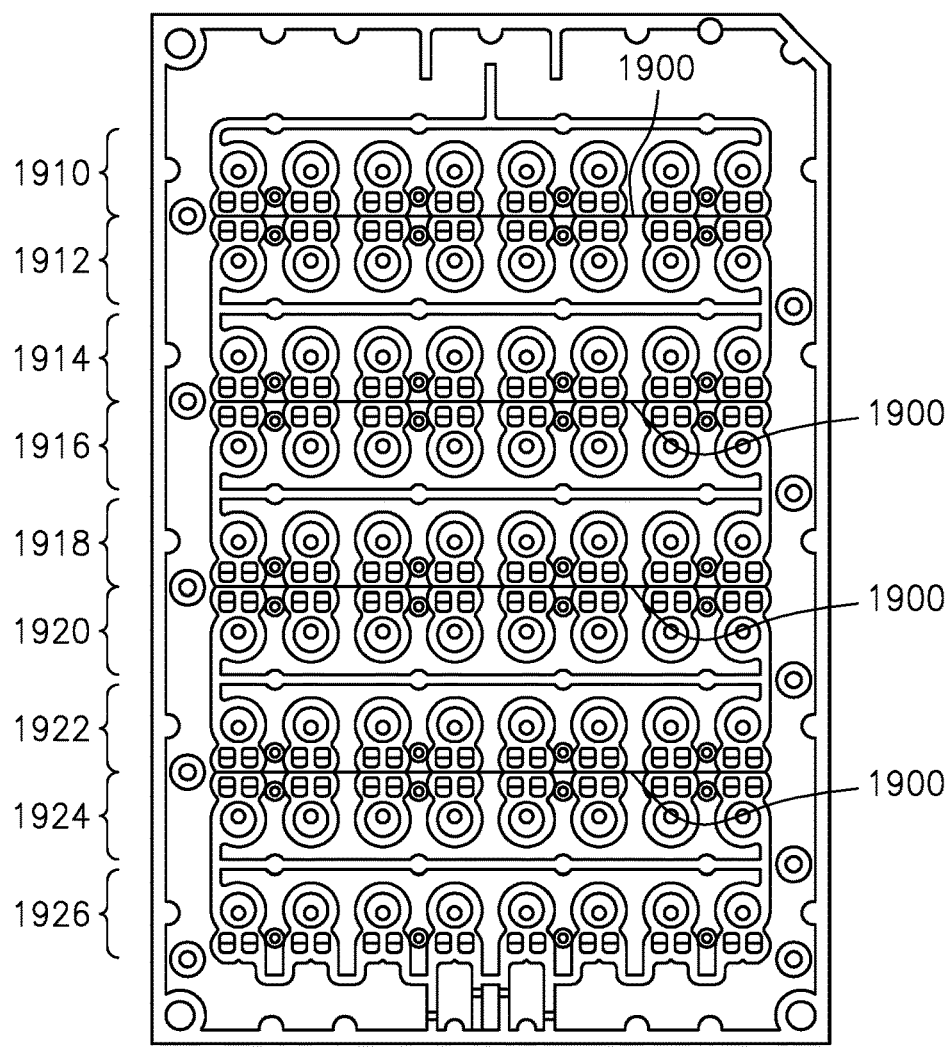
FIG. 19 is a top view of a reservoir layer of an alternative embodiment, in accordance with embodiments of the present disclosure.
Figure 19A:
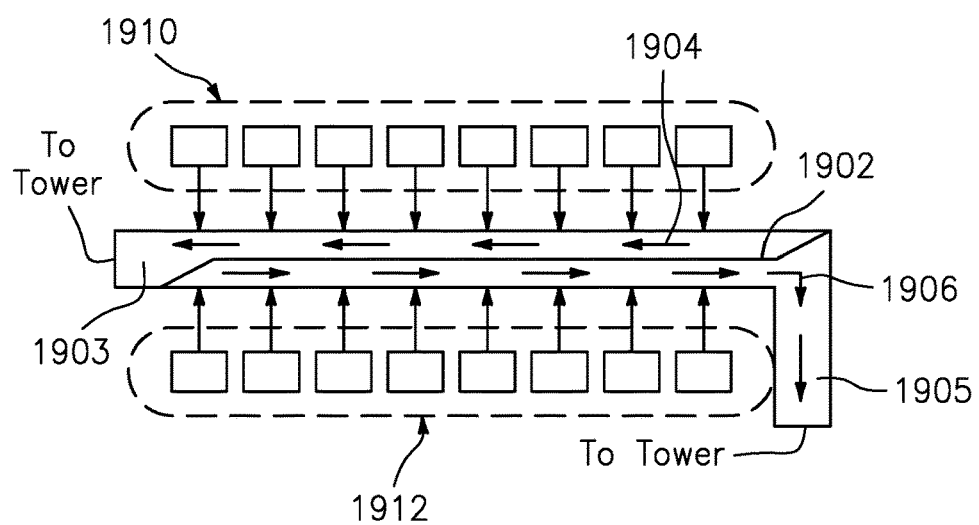
FIG. 19A is a diagram of a split waste channel of the alternative embodiment of FIG. 19, in accordance with embodiments of the present disclosure.

Referring to FIGS. 19 and 19A, the cartridge discussed herein with five (5) strips may be modified to have nine (9) assay strips 1910-1926, by splitting four of the buffer banks 402-405 in half horizontally as indicated by lines 1900 and splitting the common waste channel 810 in half to create two channels as indicated by a line 1902, one waste channel 1903 on top and one waste channel 1905 on bottom as shown in FIG. 19A. FIG. 19A shows a block diagram of 16 fluidic circuits the upper 8 circuits corresponding to one assay trip 1910, and the lower 8 circuits corresponding to the second assay strip 1912. In that case, the upper path waste 1904 would flow along the channel 1903 from the top 8 circuits (e.g., assay strip 1910) to the left tower and the lower path waste 1906 would flow along the channel 1905 from the bottom 8 circuits (e.g., assay strip 1912) to the right tower. As a result, the width of the common waste channels 810-818 may need to be widened to permit the dual flow and ensure there is not too much back pressure to pump the waste up the towers. In that case, each side would connect to its own waste tower and the 16×1 assay strips described hereinbefore would all become 8×1 assay strips 1910-1926. The last assay strip 1926 would not need to be split as it is already an 8×1 strip. While this configuration removes the redundancy of the towers shown in other design embodiments described herein, there would still be no comingling of waste from the common waste reservoir to any other assay strip.

Having fluidically isolated assay strips of the present cartridge allows a user to perform a single set of assays, e.g., 8 or 16 samples (or other number of samples), without having to run the entire cartridge. Then, at a later time or times, run another set or sets of assays, independent of the prior sets. Thus, the present disclosure permits partial assay runs or partial use or reuse or continued use of the assay cartridge, through the use of assay strips as described herein. Accordingly, the cartridge of the present disclosure provides all the benefits of existing micro-plates that permit running assays in a smaller number of wells, and multiple times with different wells each time, for a given microplate, with (at least) the further advantages of automation (less manual labor), low sample volume, and low coefficient of variation (CVs).

As described herein, the cartridge of the present disclosure is a multi-use (or reusable) cartridge for running assays on fluid samples, that allows the user to run assays (or "assay strips") using portions of the cartridge (i.e., a predetermined group of samples) at a given time, and then run assays on other portions of the cartridge at a later time. Once all the assay strips on the cartridge have been run (or used), the cartridge is no longer usable for performing assays, and may be disposed. However, if any assay strips on the cartridge have not been run, the cartridge may be stored for future use and the unused assay strips run at a later time, if desired. Also, any number of assay strips may be run at a given time. For example, assay strips 1, 3 and 5 could be run at the same time if desired. Then, at a later time, assay strips 2 and 4 could be run individually or simultaneously. In that case, in some embodiments, the easy-peel removable strips 324 would be removed for the assays being performed. Thus, the cartridge of the present disclosure is incrementally consumable and then disposable once all strips have been consumed or used.

While the present disclosure has been described for certain embodiments, it should be understood that any automated assay cartridge having assay strips that are completely separate or segmented from the other assay strips on the cartridge and that enable the cartridge to run assays on different portions of the cartridge is within the scope of the present disclosure.

Also, any sections or groups of samples may be referred to as assay strips. It is not required that the assay sections be linear strips. For example, they may be any form of group, cluster, set or collection of samples (and corresponding buffer, RA, dye wells), independent of their physical arrangement, layout or topology on the cartridge, and whether or not they are adjacent to each other, that meet the functional requirements described herein.

The 72×1 cartridge of the present disclosure can perform the same assay as a 96 well micro-plate, because typically a micro-plate uses 40 wells for the assay, 16 wells for calibration, and another 40 wells for redundancy. The cartridge of the present disclosure has built-in assay redundancy (e.g., three GNRs per assay) and is pre-calibrated (it comes with a calibration curve/table which is loaded into the instrument). Other number of assay elements or GNRs may be used if desired.

Having fluidically isolated buffer banks and a fluidically isolated common waste reservoir allows the fluidics circuits associated with each assay strip to be fluidically isolated from fluidics circuits associated with other assay strips on the same cartridge. Also, having a separate buffer bank for each assay strip allows the user to optimize the buffer solution used for each assay strip run, without any fear of comingling or cross contamination from other assay strips. Also, there may be more than one fluidically isolated separate buffer bank for a given assay strip. For example, the buffer banks may be further segregated to permit the user to use different buffers in the same assay strip if desired, e.g., as shown by a dashed line 1700 (FIG. 17). In that case, in one embodiment, vertical walls may be placed between the "pods" in a given buffer bank to create multiple separate buffer storage areas. Also, in that case, the label may have additional buffer insertion holes to permit pipetting the buffer liquid into the separate buffer banks for a given assay strip.

Also, the present disclosure is not limited to use with protein based assays, and may be used with any type of fluidic, chemical, or biochemical assay that receives input fluid and dispenses waste fluid. For example, the present disclosure may also be used with DNA based fluid assays or any other type of assay.

The instrument 1400 described herein and shown in FIG. 14 may be a computer-controlled device having the necessary electronics, computer processing power, interfaces, memory, hardware, software, firmware, logic/state machines, databases, microprocessors, communication links, displays or other visual or audio user interfaces, printing devices, and any other input/output interfaces, including sufficient optics and optical control and measurement capability and pneumatic supply capability, to provide the functions or achieve the results described herein. Except as otherwise explicitly or implicitly indicated herein, process or method steps described herein are implemented within software modules (or computer programs) executed on one or more general purpose computers. Specially designed hardware may alternatively be used to perform certain operations. In addition, computers or computer-based devices described herein may include any number of computing devices capable of performing the functions described herein, including but not limited to: tablets, laptop computers, desktop computers and the like. The computer for the instrument may be located inside or outside the physical instrument housing.

Although the disclosure has been described herein using exemplary techniques, algorithms, or processes for implementing the present disclosure, it should be understood by those skilled in the art that other techniques, algorithms and processes or other combinations and sequences of the techniques, algorithms and processes described herein may be used or performed that achieve the same function(s) and result(s) described herein and which are included within the scope of the present disclosure.

Any process descriptions, steps, or blocks in process flow diagrams provided herein indicate one potential implementation, and alternate implementations are included within the scope of the preferred embodiments of the systems and methods described herein in which functions or steps may be deleted or performed out of order from that shown or discussed, including substantially concurrently or in reverse order, depending on the functionality involved, as would be understood by those reasonably skilled in the art.

It should be understood that, unless otherwise explicitly or implicitly indicated herein, any of the features, characteristics, alternatives or modifications described regarding a particular embodiment herein may also be applied, used, or incorporated with any other embodiment described herein. Also, the drawings herein are not drawn to scale, unless indicated otherwise.

Conditional language, such as, among others, "can," "could," "might," or "may," unless specifically stated otherwise, or otherwise understood within the context as used, is generally intended to convey that certain embodiments could include, but do not require, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment.

Although the invention has been described and illustrated with respect to exemplary embodiments thereof, the foregoing and various other additions and omissions may be made therein and thereto without departing from the spirit and scope of the present disclosure.

What is claimed is:

1. A microfluidic device for conducting a fluid assay, comprising: a fluidics layer having at least one micro-fluidic channel configured to allow assay fluids to flow there-along, the channel having channel side walls and a channel bottom, the channel having a channel geometry;
   wherein the microfluidic channel has at least one channel feature portion, comprising a valve feature or a piston feature;
   and wherein all surfaces of the fluidics layer being made from injection-molded optically clear liquid PDMS.

2. The microfluidic device of claim 1, wherein the channel geometry comprises at least one of: rounded bottom, rounded sides, and spherical shape.

3. The microfluidic device of claim 1, wherein the microfluidic channel having a channel height and channel width and having at least one microfluidic valve seat disposed on the channel bottom, the valve seat having a geometry comprising at least one of: oval, rounded, square, and flat-top triangle.

4. The microfluidic device of claim 3, wherein the valve seat having a height that is below the channel height.

5. The microfluidic device of claim 1, wherein the channel has a channel width of less than about 125 microns.

6. The microfluidic device of claim 1, wherein there are a plurality of microfluidic channels, at least two of the channels having a spacing distance therebetween of about 1.5 mm to about 200 microns.

7. The microfluidic device of claim 1, wherein the feature portion has a depth or geometry that is different from the rest of the channel.

8. The microfluidic device of claim 1, wherein the microfluidic channel has a channel height and channel width, and wherein at least one of the channel width and the channel height being varying in value.

9. The microfluidic device of claim 8, wherein the channel is configured as a channel-type filter which traps particles or cells.

10. The microfluidic device of claim 1, further comprising at least one flow element in fixed position in the channel and a flexible membrane layer bonded to a top side of the fluidics layer, a portion of the flexible membrane layer configured to deflect into or away from the channel due to pneumatic pressure applied to one side of the membrane portion to actuate at least one of a valve and a piston.

11. A method of making a microfluidic device for conducting a fluid assay, comprising: injecting optically clear liquid PDMS into a mold template having at least one microfluidic channel and at least one channel feature disposed in the mold template, to form a fluidics layer;
    removing the fluidics layer from the mold template;
    placing the fluidics layer on a non-stick surface during curing of the fluidics layer, the non-stick surface allowing the fluidics layer to shrink as it cures, thereby ensuring final dimensions of the fluidics layer meets predetermined tolerances;
    and wherein all surfaces of the fluidics layer are made from injection-molded optically clear liquid PDMS.

12. The method of claim 11, further comprising:
    inserting at least one flow element into the channel; and
    attaching a flexible membrane layer to a top side of the fluidics layer.

13. The method of claim 12, further comprising attaching a relatively rigid backing surface to a bottom side of the fluidics layer before the inserting step.

14. The method of claim 13, further comprising attaching a relatively rigid reservoir layer to the membrane layer after the step of attaching the membrane layer to the fluidics layer, the reservoir layer having pneumatic channels disposed on an underside of the relatively rigid plastic reservoir layer, the flexible membrane layer configured to deflect due to pneumatic pressure applied along the pneumatic channels to one side of the membrane portion to actuate at least one of a valve and a piston.

15. The method of claim 13, wherein the relatively rigid backing surface is removable, and further comprising removing the relatively rigid backing surface from the bottom side of the fluidics layer.

16. The method of claim 11, wherein the fluidics layer has a thickness of about 1.1 mm.

17. The method of claim 11, wherein the at least one feature is a valve feature or a piston feature.

18. The method of claim 11, wherein the non-stick surface comprises surface-coated Teflon.

19. A microfluidic device for conducting a fluid assay, comprising: an injection-molded fluidics layer having at least one microfluidic channel configured to allow assay fluids to flow there-along, the fluidics layer being made from injection-molded optically clear liquid PDMS; at least one flow element in fixed position in the channel; a flexible membrane layer bonded to a top side of the fluidics layer, a portion of the flexible membrane layer configured to deflect into or away from the channel due to pneumatic pressure applied to one side of the membrane portion to actuate at least one of a valve and a piston; and wherein all surfaces of the fluidics layer are made from injection-molded optically clear liquid PDMS.

20. The microfluidic device of claim 19, wherein the channel has a channel height and a channel bottom, and has at least one microfluidic valve seat in the channel that engages with the flexible membrane to form the valve, the valve seat having a height that is below the channel height.

* * * * *